(12) United States Patent
Honig

(10) Patent No.: US 10,111,733 B2
(45) Date of Patent: Oct. 30, 2018

(54) DEVICE, SYSTEM AND METHOD FOR PROSTHODONTIC RESTORATION

(75) Inventor: Iulian Honig, Bucharest (RO)

(73) Assignee: ABRACADABRA IMPLANTS LTD, Bat Yam (IL)

( * ) Notice: Subject to any disclaimer, the term of this patent is extended or adjusted under 35 U.S.C. 154(b) by 422 days.

(21) Appl. No.: 14/234,637

(22) PCT Filed: Jul. 26, 2012

(86) PCT No.: PCT/IB2012/053829
§ 371 (c)(1),
(2), (4) Date: Jan. 24, 2014

(87) PCT Pub. No.: WO2013/014643
PCT Pub. Date: Jan. 31, 2013

(65) Prior Publication Data
US 2014/0170597 A1    Jun. 19, 2014

Related U.S. Application Data
(60) Provisional application No. 61/512,174, filed on Jul. 27, 2011.

(51) Int. Cl.
*A61C 8/00* (2006.01)
*A61C 13/00* (2006.01)
*A61K 6/08* (2006.01)

(52) U.S. Cl.
CPC ............ *A61C 8/0053* (2013.01); *A61C 8/006* (2013.01); *A61C 8/0016* (2013.01); *A61C 8/0068* (2013.01); *A61C 8/0069* (2013.01); *A61C 13/0006* (2013.01); *A61K 6/08* (2013.01)

(58) Field of Classification Search
CPC ..... A61C 8/0048; A61C 8/005; A61C 8/0053; A61C 8/0057; A61C 8/0063
See application file for complete search history.

(56) References Cited

U.S. PATENT DOCUMENTS

| 3,732,621 | A | | 5/1973 | Bostrom |
| 4,645,453 | A | | 2/1987 | Niznick |
| 4,932,868 | A | * | 6/1990 | Linkow ............... A61C 8/0018 433/174 |
| 5,178,539 | A | * | 1/1993 | Peltier .................. A61C 8/005 433/173 |
| 5,520,540 | A | | 5/1996 | Nardi et al. |

(Continued)

FOREIGN PATENT DOCUMENTS

| DE | 20 2006 012 016 | 12/2006 |
| FR | 2085013 | 12/1971 |
| WO | 1992/010145 | 6/1992 |

OTHER PUBLICATIONS

International Search Report and Written Opinion of International Application PCT/IB2012/053829, dated Jan. 30, 2013.

*Primary Examiner* — Edward Moran
(74) *Attorney, Agent, or Firm* — The Law Office of Joseph L. Felber

(57) ABSTRACT

This disclosed subject matter relates to dental implants in general, and in particular to dental implants having an abutment for mounting a prosthodontic restoration thereon, wherein the abutment is customizable and/or adjustable that may be configured according an individual's morphology, clinical situation and related prosthodontic requirements.

20 Claims, 22 Drawing Sheets

(56) References Cited

U.S. PATENT DOCUMENTS

| | | | | |
|---|---|---|---|---|
| 5,816,809 A | * | 10/1998 | Sapkos | A61C 8/005 433/172 |
| 5,873,721 A | * | 2/1999 | Willoughby | A61C 8/0001 433/172 |
| 7,214,063 B2 | * | 5/2007 | Cohen | A61C 8/005 433/173 |
| 2008/0261176 A1 | * | 10/2008 | Hurson | A61C 8/0022 433/174 |
| 2009/0202962 A1 | * | 8/2009 | Xam-Mar Mangrane | A61C 8/005 433/173 |

* cited by examiner

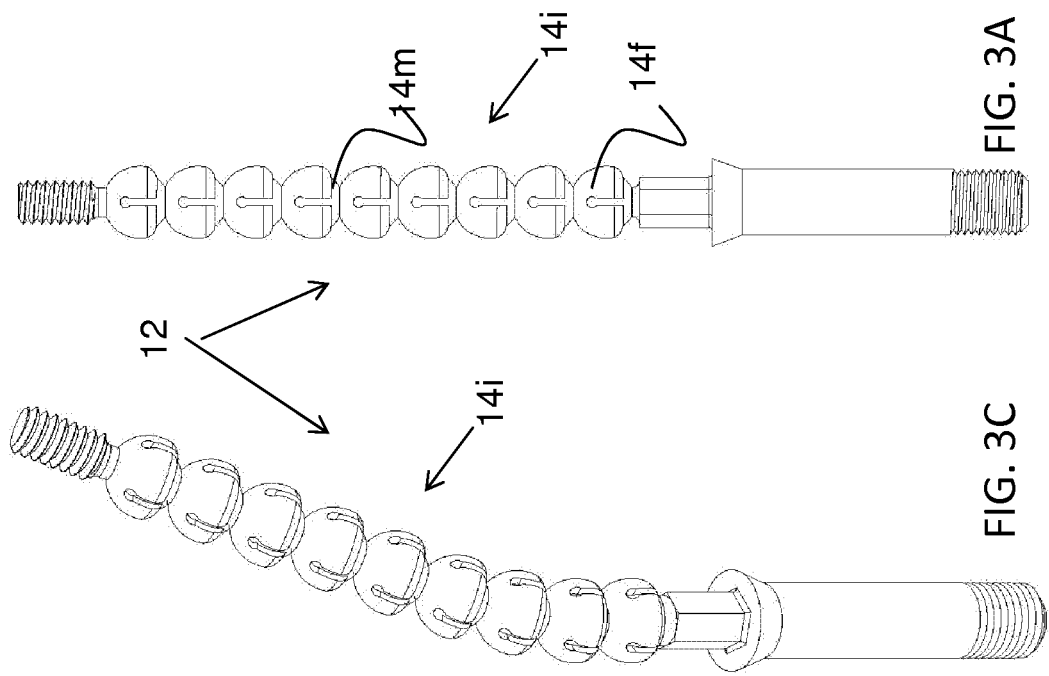
FIG. 3A
FIG. 3C
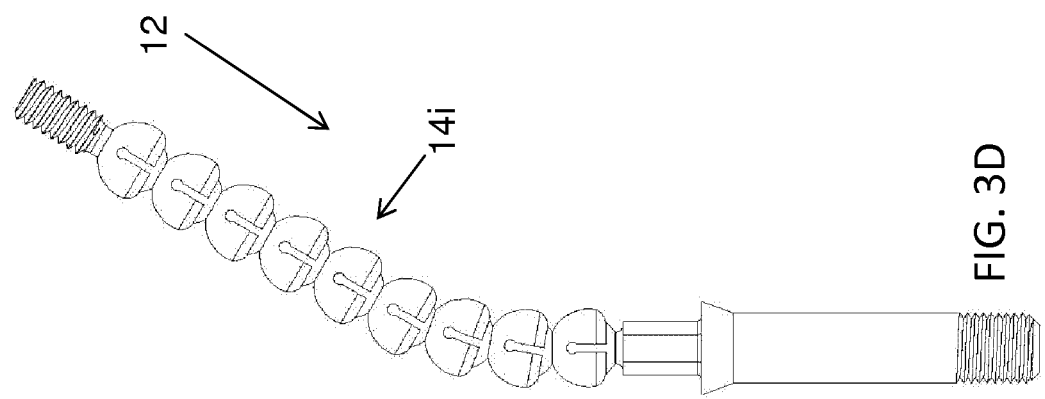
FIG. 3D
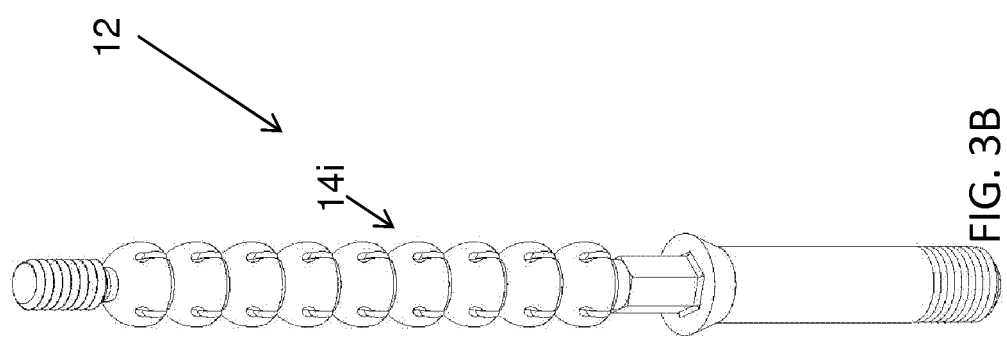
FIG. 3B

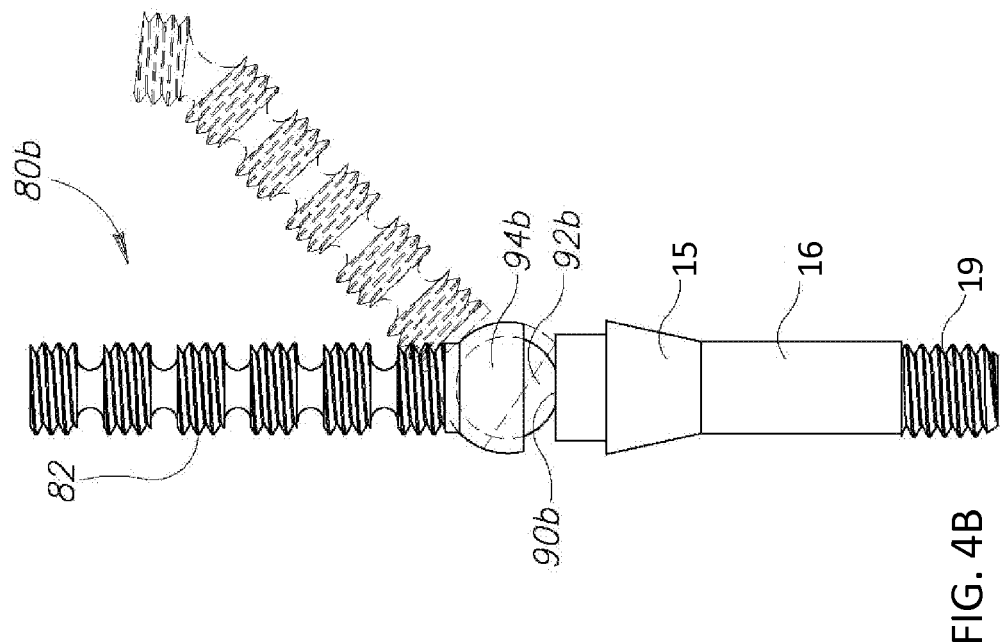
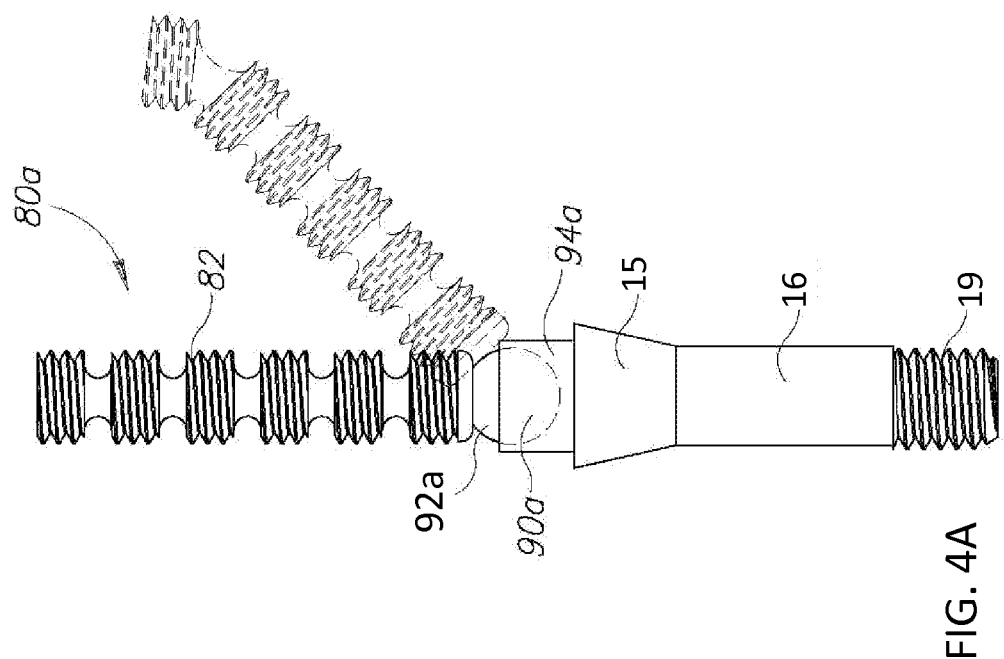

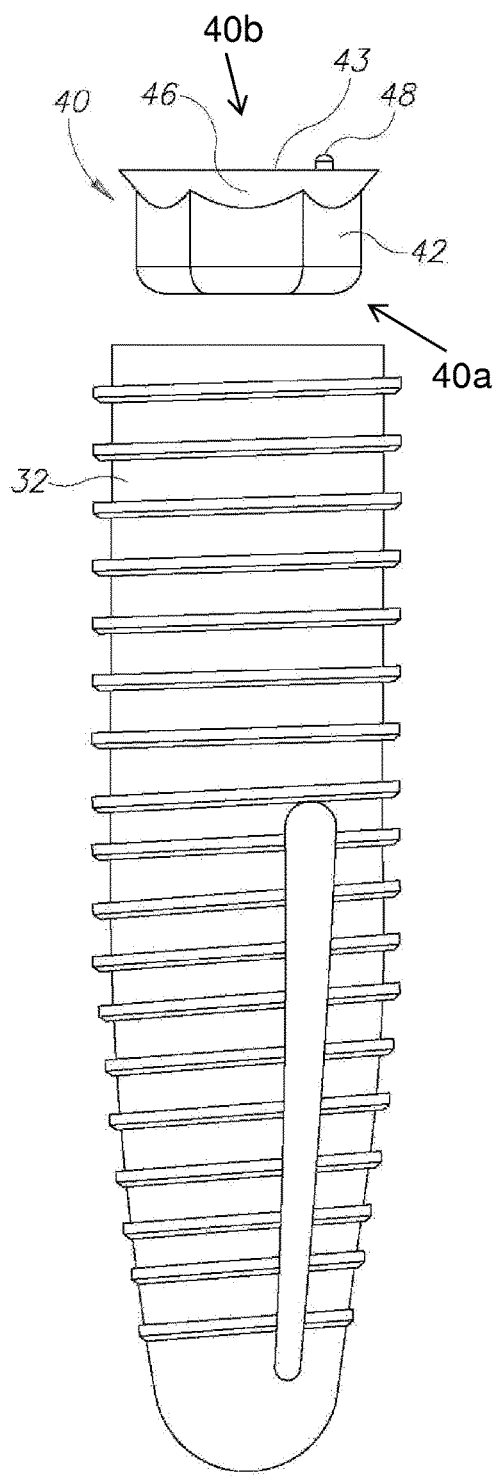
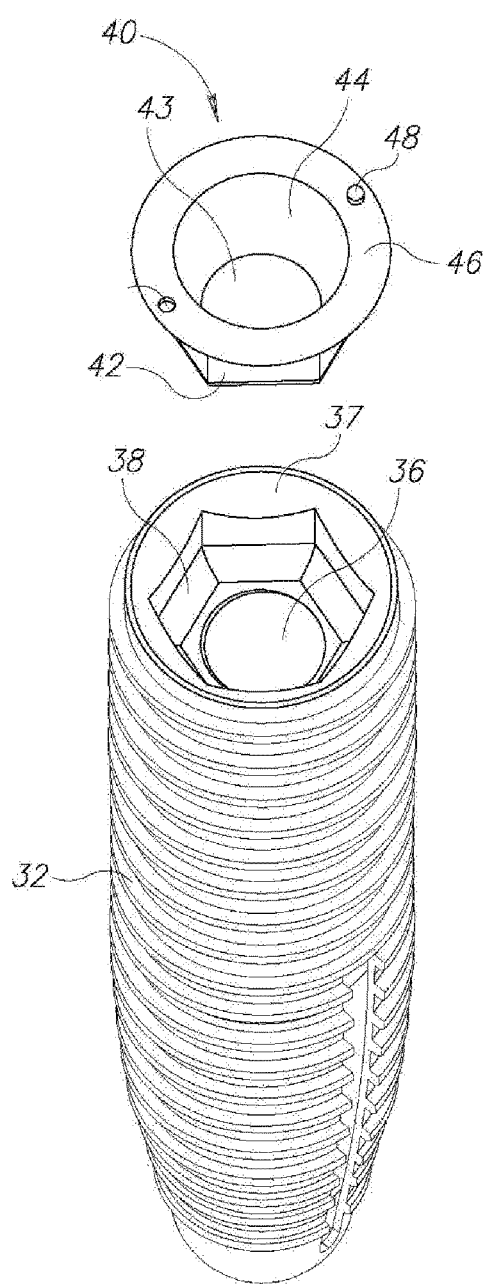
FIG.7A
FIG.7B

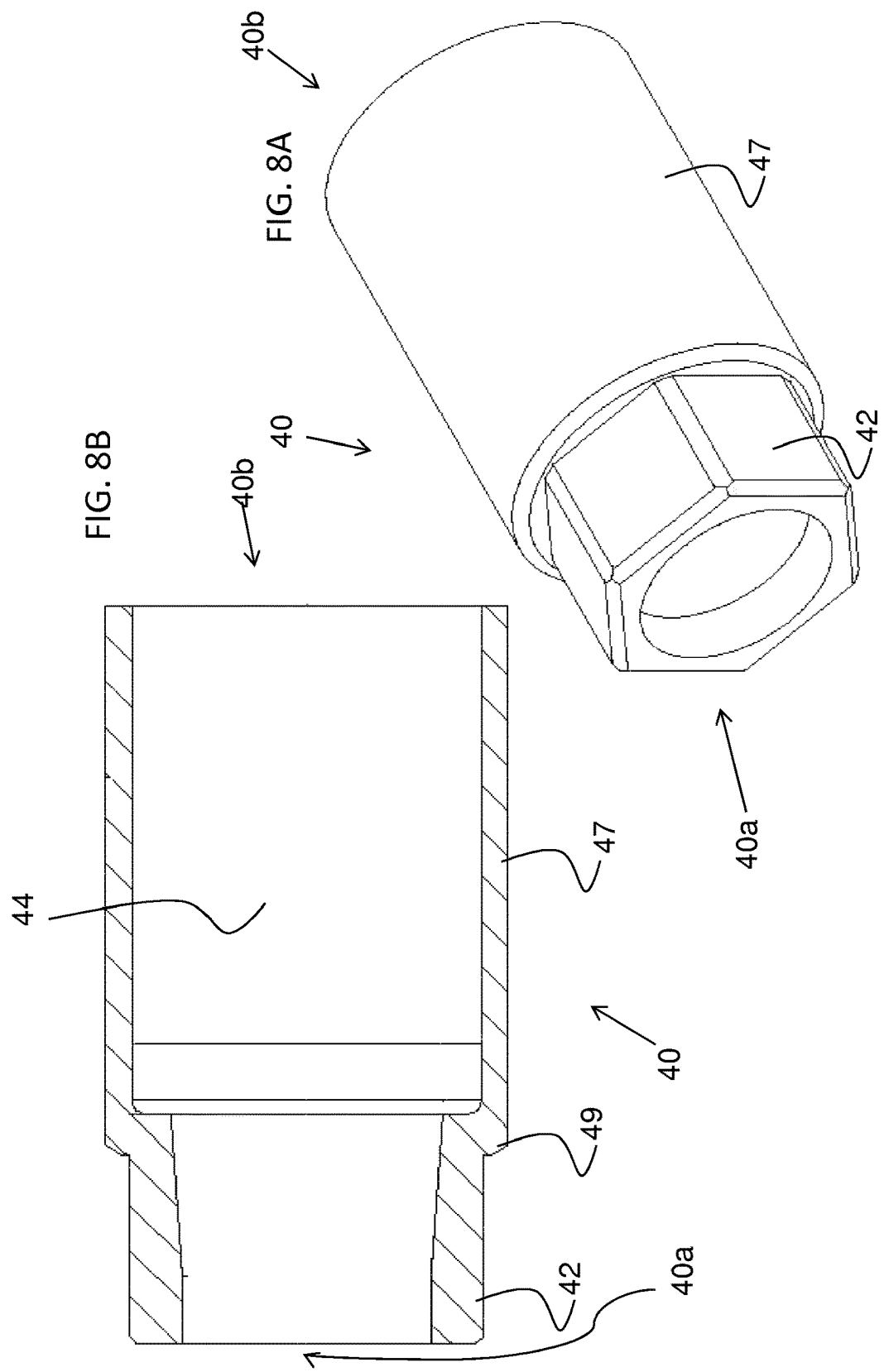

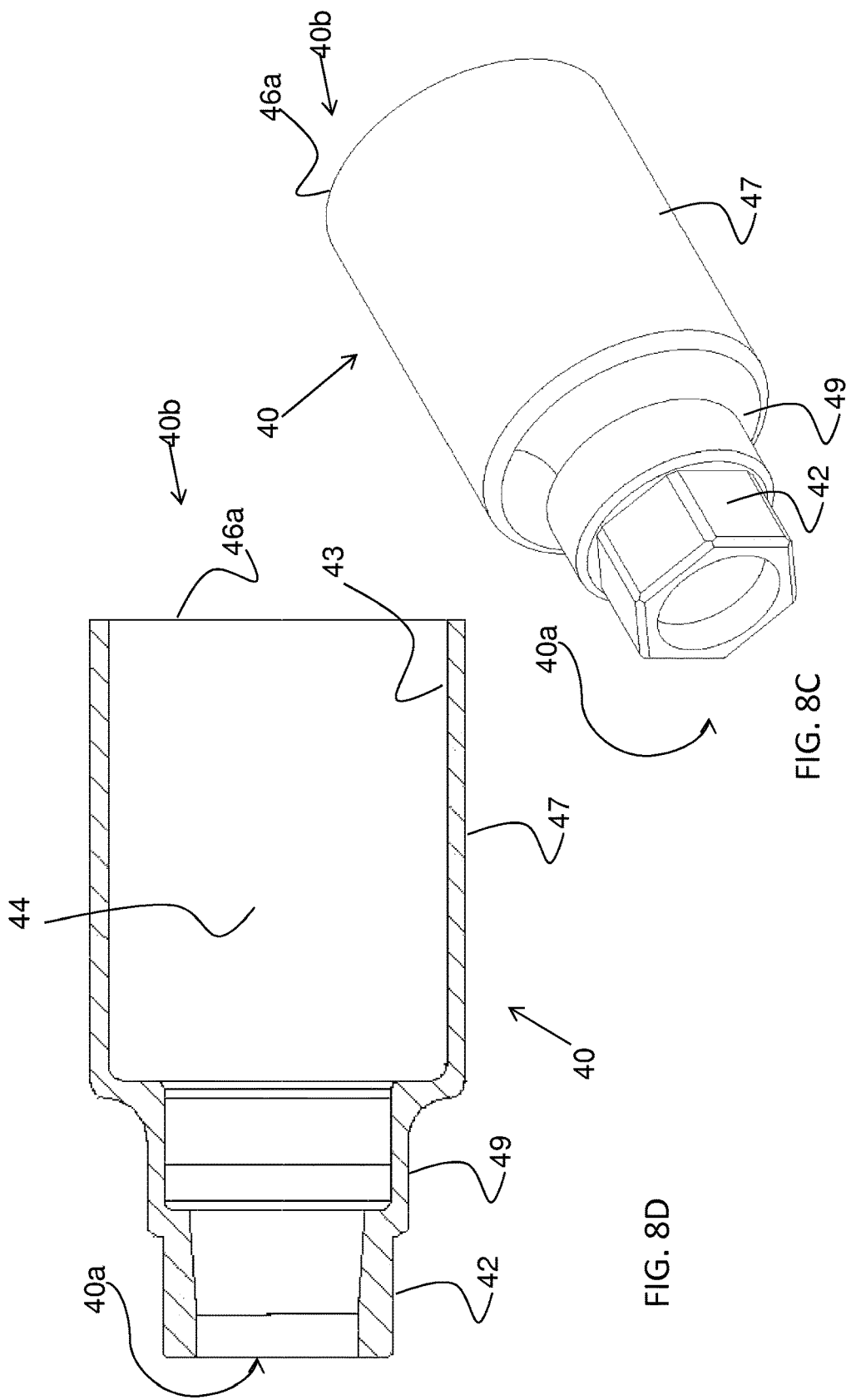

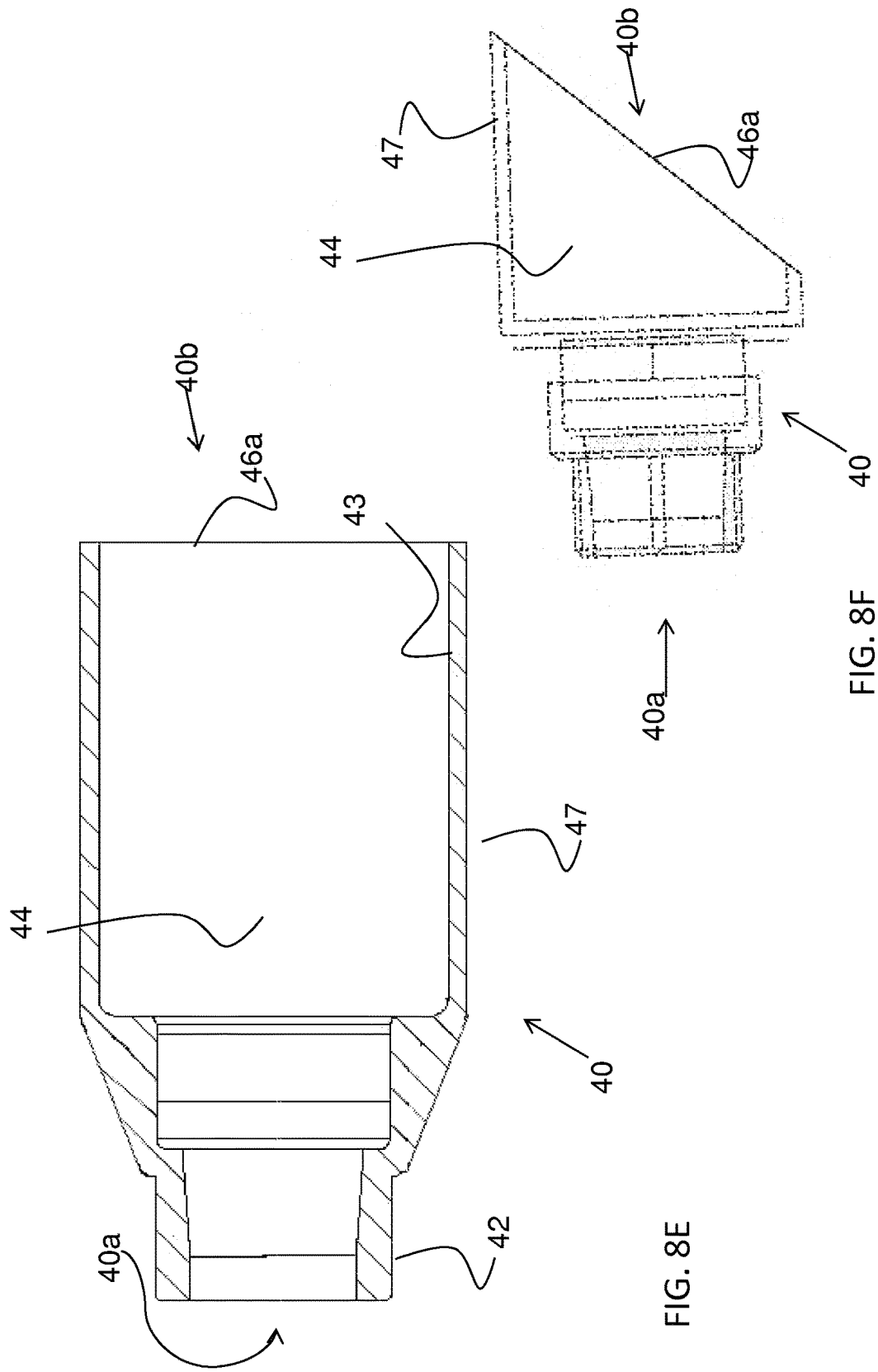

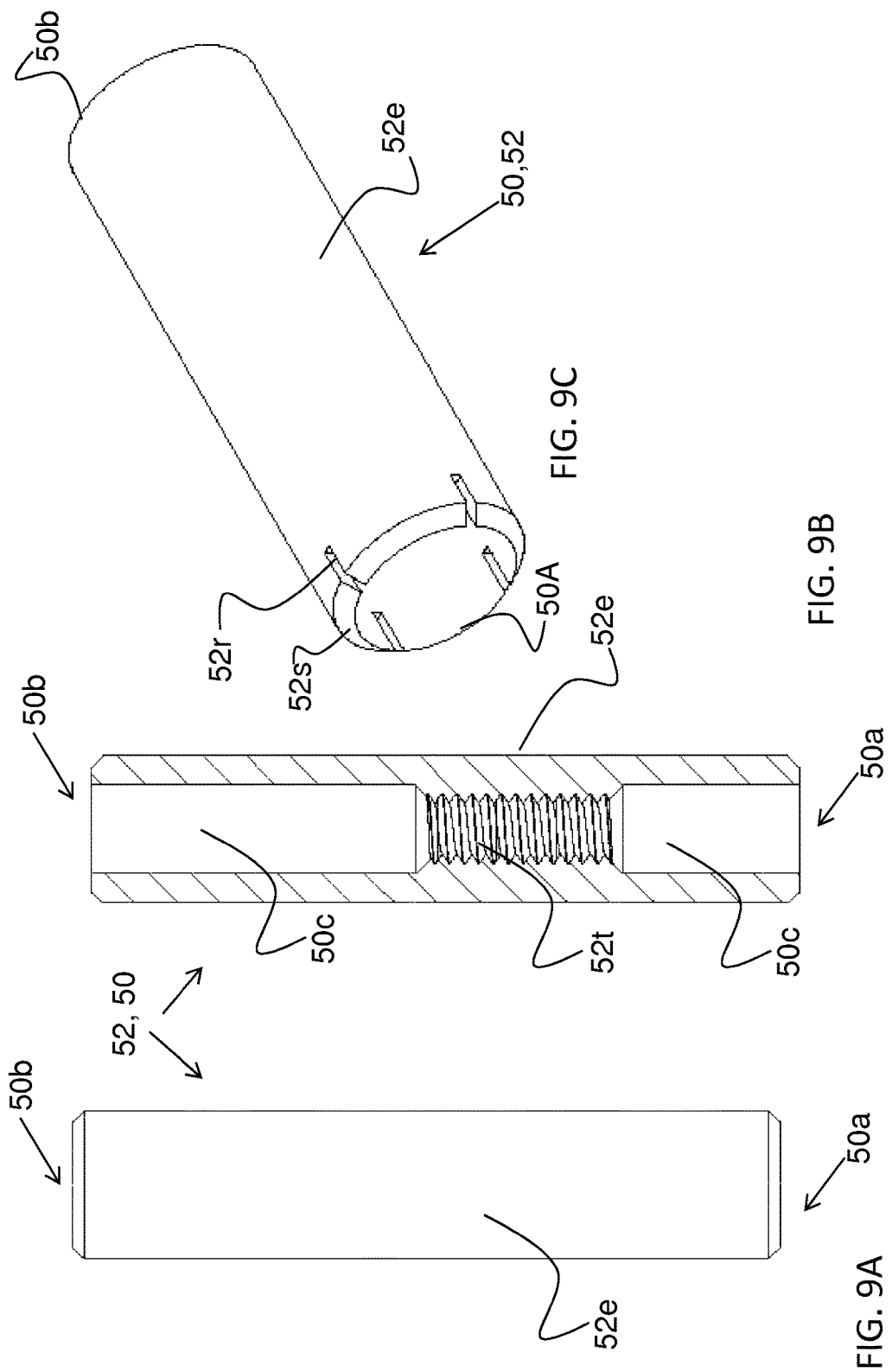

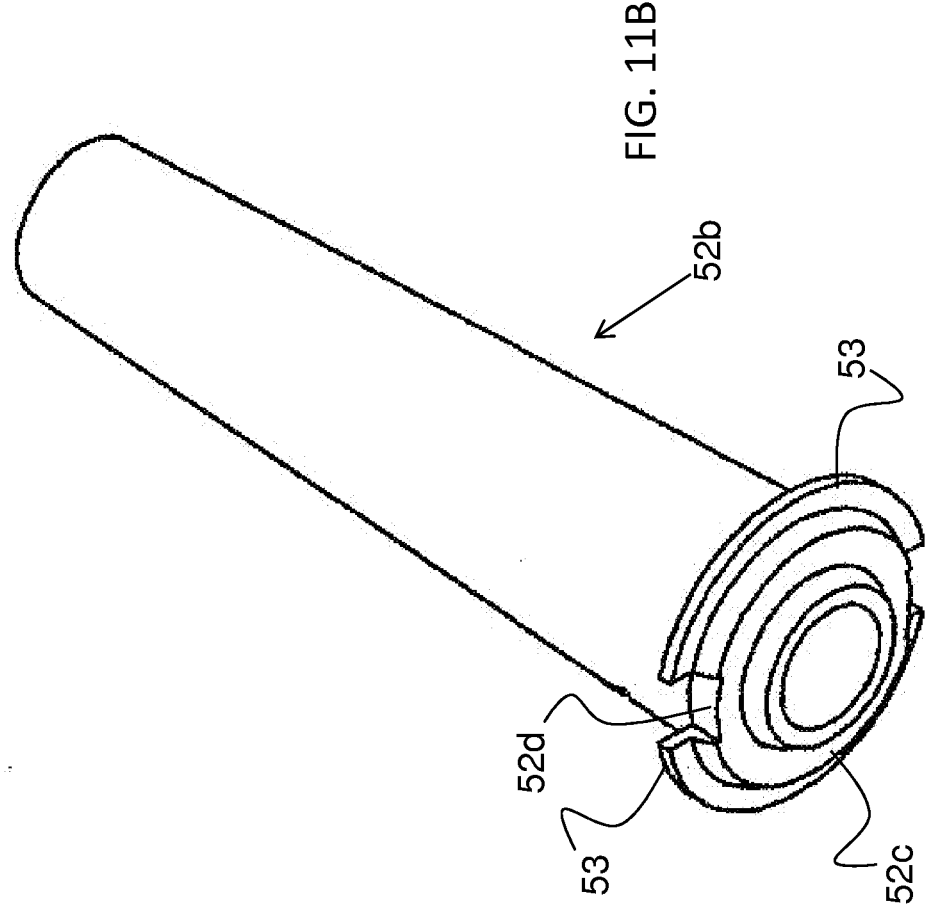
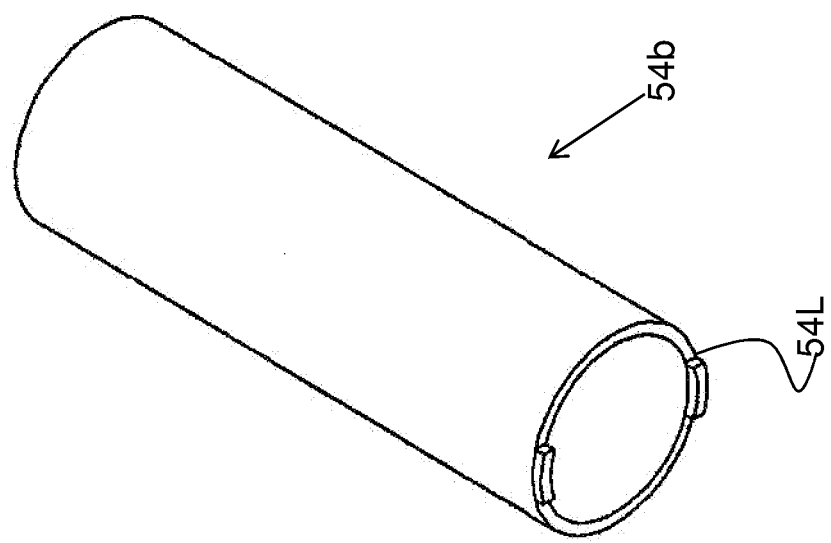

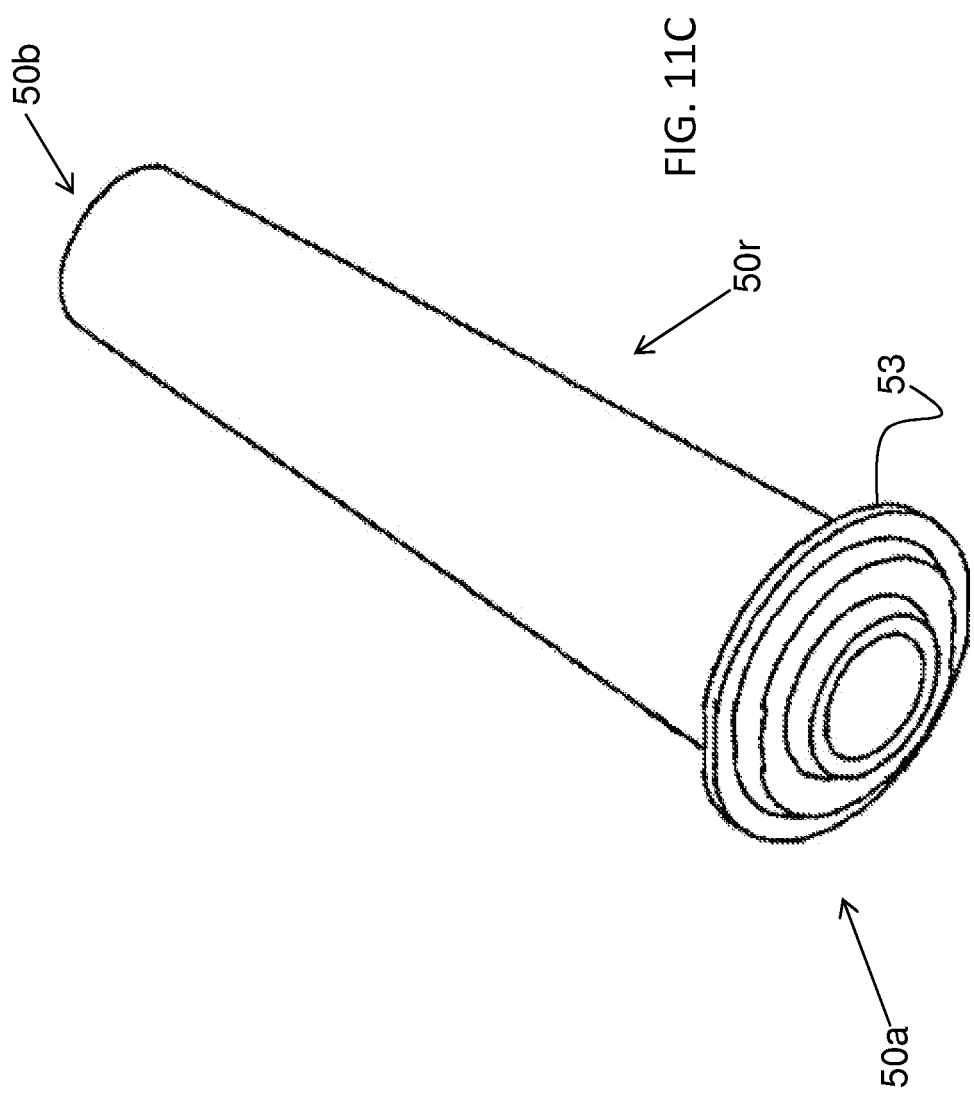

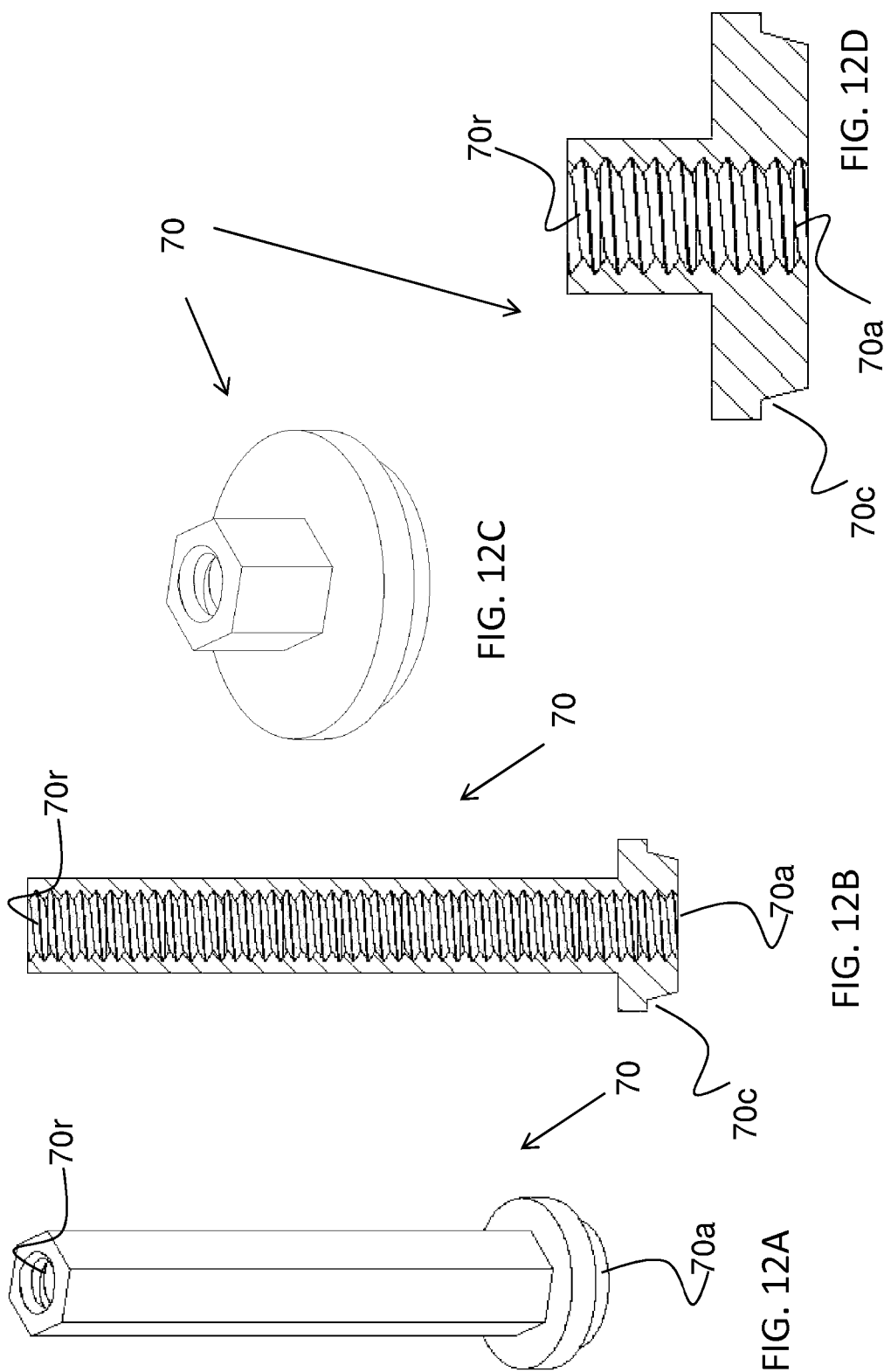

DEVICE, SYSTEM AND METHOD FOR PROSTHODONTIC RESTORATION

This Application is a national phase of, and claims priority from, PCT Application No. PCT/2012/053829, filed on Jul. 26, 2012, which claims priority from U.S. Provisional Application No. 61/512,174, filed Jul. 27, 2011, which is hereby incorporated by reference as if fully set forth herein.

FIELD OF THE DISCLOSED SUBJECT MATTER

This disclosed subject matter relates to dental implants in general, and in particular to dental implants having an abutment for mounting a prosthodontic restoration thereon.

BACKGROUND OF THE DISCLOSED SUBJECT MATTER

Dental implants are known in the art and typically include a dental anchor securely inserted into or onto the patient jawbone, and an abutment member mountable to the dental anchor, for coupling a prosthodontic restoration thereon. Commonly, in the art, the abutment is affixed to the anchor through a fixation screw also known as an abutment screw.

A multitude of prefabricated abutments and implant systems of various designs are offered to clinicians in an effort to provide clinicians with necessary means to successfully restore edentulous patients.

In order to be successful, the implant and all prosthodontic restorative devices associated therewith, in particular those used on the implant, must meet specific functional, biological and esthetic requirements. These requirements may be achieved when the restorative implant system, and devices used on the implants, adhere to 8 biomechanical principles, including: 1. Preservation of implant structure; 2. Passive retention and passive support; 3. Resistance form; 4. Structural durability of the restoration; 5. Marginal integrity; 6. Retrievability; 7. Preservation of the perio-implant tissues; 8. Individuality; Therefore, for a successful implant procedure to take place, the above mentioned biomechanical principles must be met to achieve the implant requirements including functional requirements, biological requirements and esthetic requirements.

A number of factors in the design of the abutments and the restorative implant systems, for example abutment's geometry, shape, position and the connection to anchor system, determine if a restoration can adhere to mentioned biomechanical principles in order to achieve the desired functional, biological and esthetic requirements.

Prior art abutments and restorative systems do not meet these bio mechanical principals, leading to major drawbacks in the implants utilized today. These drawbacks cause clinicians to compromise the functional, biologic and esthetic requirements of the restoration. Restorative systems that do not adhere to the biomechanical principles, shorten the survivability and/or viability of the implant, necessitate: laborious maintenance, additional surgeries, determines reduced implant system functionality, poor esthetics and irreparable damage to host tissues.

One prior art Patent regarding abutment attempt to control the position of the abutment as described in U.S. Pat. No. 4,645,453 to Niznick discloses an implant system which includes an anchor, the accessible end of which is located substantially at the level of the gum tissue at the alveolar crest. A bendable adapter made of titanium or titanium alloy has one end inserted into the accessible anchor socket for rigid connection thereto, and a second distal end projecting into the dental crown region to support a superstructure. The projecting part of the adapter may take various forms. It may provide a simple coping upon which a single tooth replacement may be built, or it may provide a socket for connection to companion structures. The intermediate portion of the adapter is necked down to provide a bendable region close to the level of the gum tissue whereby the anchor can be positioned for maximum retention, and the projecting end can be positioned to avoid tissue interference, to achieve parallelism for detachable connectors, to achieve maximum occlusal and esthetic functions.

Furthermore current implant anchor systems are devoid of uniformity and standardization such that the different anchors are incompatible with one another's abutment. Such incompatibility between different implant system manufacturers lead to increased cost and lack of standardization.

SUMMARY OF THE DISCLOSED SUBJECT MATTER

Current implants systems provide abutments with limited positioning capabilities and therefore lack control of abutment angulations, directionality and length. Similarly, current abutments do not provide parallelism between abutments and/or residual teeth. Limited positioning and/or parallelism of abutment in relation with adjacent and/or opposite abutments or teeth determine multiple active paths of insertion and retrievability thus disrupting the principles of passive retention, passive support and resistance form.

Further examples, of drawbacks associated with the current implant systems are: the disrupted shape of abutment due the formation of undercuts and/or irregularities while additional adjustments are needed (by filing and/or casting) to improve abutment's position, causing incomplete seating of restoration to abutment thus poor retention and lower durability of restoration; the unstable connection systems and related gaps between the different implant system parts (for example between the anchor and abutment) that may lead to percolation and retention of fluids and pathogens into implant structure about the vicinity of host tissue, irritation inflammation and damage to perio-implant tissue, bad odor, bad taste, and damage to implant's elements and/or structure; devoid of a finish line resulting in weak, over contouring restoration margins which intrude perio implant tissues, increasing food and plaque retention; limited standard options of prefabricated finish lines which does not account individual morphology and prosthodontic requirements; impossibility to adjust the height of the transmucosal portion of the abutment according individual morphology of biologic width and individual prosthodontic requirements.

Perhaps most importantly, current implant may further require a multi stage procedure and multiple surgeries to complete a single implant procedure.

Furthermore, current restorative systems lack retrievability, for example, if an element of state of the art abutments is damaged it cannot be replaced with a new one while fitting with the restoration in use, thus, a new restoration has to be manufactured, fabricate.

The present invention overcomes the deficiencies of the background by providing a prosthodontic implant system and method that provides a customizable and/or adjustable implant abutment assembly that may be configured according the individual's morphology, clinical situation and related prosthodontic requirements allowing a clinician to adhere the aforementioned biomechanical principles, including: 1. Preservation of implant structure; 2. Passive Retention and passive Support; 3. Resistance form; 4. Structural durability of the restoration; 5. Marginal integrity; 6. Retrievability; 7. Preservation of the period-implant tissues; and; 8. Individuality.

Therein the abutment assembly of the present invention provides for facilitating and allowing a practitioner to meet the individual's different requirements including biologic, aesthetic and functional requirements.

Most preferably an adjustable implant abutment allows the practitioner to realize and meet the biomechanical principles relative to a patient's individual morphology. Optionally and preferably the adjustment of the abutment system provides an abutment assembly that may be adjusted to a desired position, required geometry and shape. Optionally and preferably the adjustment of the abutment system provides an abutment assembly that further provides for: a stable abutment to anchor connection, eliminates gaps, enables clinicians to adjust and shape the transmucosal portion of the abutment, provides for the formation of an accurate finish line, ensures abutment to restoration marginal fit, standardizes affixing methods, eliminate abutment shaft and fixation screw related deficiencies, provides a fully retrievable restoration and enables abutment replacement. Optionally, the adjustable abutment assembly may be compatible with any state of the art implant systems and specifically implant anchors.

Most preferably customization and adjustment of the abutment assembly allows a practitioner to adhere to the biomechanical principles while ensuring the implant outcomes meet the functional requirements, biological requirements and esthetic requirements.

Most preferably the adjustable and customizable abutment according to optional embodiments of the present invention provide an abutment assembly that may be adjusted in real time by the practitioner and/or operator, according the individual's morphology, requirements and clinical situations.

Optionally and preferably, the adjustable abutment according to the present invention provides an abutment that can match and meet the large diversity of implant anchors known in the art, and may optionally be mounted in one surgical procedure and one stage.

Optionally and most preferably, the abutment assembly according to the present invention may be adjusted and shaped to form a smooth, well defined and contoured finish line.

A well defined finish line is an essential component in ensuring the success of the implant process as it governs many of the biomechanical principles. Most preferably a proper finish line provides for: structural durability of restoration, closely fitting and/or coupling the abutment with the restoration's margins, defines the platform for satisfactory restoration thicknesses (ensuring that the thickness of the abutment corresponds with the thickness of the restoration).

A proper finish line further provides for ensuring that the abutment emerges with restoration's profile, therein creating an "emerging profile" without over contouring that in turn prevents percolation of fluids, irritation of perio-implant tissues, plaque retention and gingival inflammation.

A well defined finish line may be contoured to assume the optimal orientation and positioning, such that the finish line is positioned parallel with the occlusal plane and perpendicular to abutment axis, most preferably to passively interface the forces encountered by the implant and host tissue. Therefore the more nearly perpendicular the finish line, the more passive the support and the greater the resistance form. Therefore the more nearly parallel the finish line, the more passive the retention and the greater the resistance form.

Other distinct advantages offered by the adjustable abutment according to the present invention in the creation of a customizable finish line, relates to its position, affording improved preservation of perio-implant tissue. Preferably the finish line is positioned slightly above the gingiva, in a region that is easy to clean and inspect, thus, substantially diminishing the risk of inflammatory response. Preferably the finish line is positioned sufficiently remote from the alveolar bone to preserve at least 2 mm of combined epithelial and connective tissue attachment ("biologic width".), thus preventing bone loss and assuring bone support.

A further advantage offered by the adjustable abutment assembly according to the present invention most preferably provides control of the transgingival portion of the abutment. In order to preserve the perio implant tissue, preferably, the diameter of the transgingival portion of abutment must be smaller than the anchor's diameter, allowing crestal bone to over-contour the anchor's platform therein providing for platform switching, thus improving the anchor's bone support and seal, the mucosal seal and prevent alveolar bone resorption.

Accordingly optional embodiments of the present invention provide for controlling the abutment diameter relative to the anchor's diameter.

Most preferably in order to adhere to the biomechanical principles the abutment assembly most preferably should be adjusted to be substantially perpendicular the occlusal plane and just about parallel with adjacent abutments and/or teeth. Thus essentially defining only one path of insertion and retrievability that is substantially parallel to the axis of the abutment. That provides the restoration with complete sitting, and the restoration margins to passively lie against and closely fit with the finish line. This in turn synergistically increases retention and resistance form, and determines that the implant structures, the implant elements and perio implant tissues are not subject to tension.

By allowing the creation of one path of insertion and retrievability most preferably the adjustable abutment according to the present invention, provides for passive retrievability and retrofitting of a restoration. This provides for the maintenance of the implant for example including but not limited to, performance of additional surgical procedures, replacement of the abutment or prosthodontic elements, exercise hygienic evaluation, to allow for the adjustment of the restoration in case an implant is lost, or the like.

Most preferably, the adjustable abutment assembly according to the present invention, provides a stable, rigid and secure connection between the abutment assembly and optional anchors.

Within the context of this application the term adjustment is to refer to any manipulation or changed and/or customization to a given structure or member thereof for example including but not limited to changing, tilting, height adjustment, filing, cutting, shaping, forming, bending, or the like. Optionally adjustments may be made with tools, conventional tools and/or dedicated proprietary tools.

Within the context of this application the term abutment and abutment assembly may be used interchangeably.

Within the context of this application the term pivot and abutment pivot and post assembly may be used interchangeably.

Within the context of this application the term occlusal plane and/or occlusal end refers to that portion of the abutment and/or abutment member positioned or directed toward the coronary portion of a tooth.

Within the context of this application the term apical plane and/or apical end refers to that portion of the abutment and/or abutment member positioned and/or directed toward the apex of the tooth, for example toward the root.

Within the context of this application the term prosthodontic requirements refers to the biologic requirement, aesthetic requirement and functional requirements that adhere to the biomechanical principles most preferably to ensuring a proper restoration outcome with respect to the individual's morphology and/or clinical situation.

Within the context of this application the term angle refers to the angle assumed by the abutment according to the present invention, by way of customization and/or adjustment, with respect to and/or in relation to the occlusal plane, implant's anchor axis and/or mounting member and/or alveolar bone and/or adjacent teeth, abutment, restoration, on the same and/or opposite jaw.

Within the context of this application the term direction refers the direction assumed by the abutment of the present invention, by way of customization and/or adjustment, wherein the direction is defined by a projection of the abutment within any of the 360 degrees of the occlusal plane.

Within the context of this application the term position refers to the spatial disposition of the abutment of the present invention, by way of customization and/or adjustment, derived and/or depicted by the angle, direction, and distance between adjacent anatomical structures for example including but not limited to tongue, lips, or the like.

The presently disclosed subject matter relates to an implant abutment assembly for mounting thereon a prosthodontic restoration. The abutment assembly includes an adjustable abutment pivot for affixing, coupling and/or associating with at least one or more of composite materials, abutment assembly elements, a prosthodontic restoration, and an interface member for interfacing with an implant anchor. The adjustable abutment pivot allows for adjusting and/or customizing the pivot to the desired angle, direction and vertical dimension so as to provide the appropriate alignment of the abutment to achieve the biologic, aesthetic and functional requirements.

Most preferably the abutment pivot comprises a pivot occlusal portion extending from a pivot mounting portion. Most preferably the abutment pivot comprises a pivot mounting portion defined about the apical end of the abutment pivot. Most preferably pivot occlusal portion defined about the occlusal end of the abutment pivot.

Most preferably pivot mounting member provides for mounting the abutment pivot with an implant anchor. Optionally and preferably pivot mounting portion may be provided in a plurality of optional forms for example including but not limited to threading, snap fit, Morse angle coupling, male-female couplers or the like.

Optionally the pivot's occlusal portion according to the present invention may be provided in a plurality of optional configurations for example including but not limited to ball and socket joint, joints, elastic rod, malleable rod, interlocking joints, elastic spring, spring member or the like.

Optionally and preferably the abutment pivot may include at least one engageable portion provided about the pivot occlusal portion. Optionally and preferably engageable portion provides for coupling with an abutment structure mounted on the adjustable pivot portion for holding the prosthodontic restoration thereon. Optionally and preferably the abutment structure engages with the engageable portion when mounted on the adjustable post.

Optionally an abutment structure may for example include but is not limited to a sleeve and/or reinforcing sleeve that may be mounted about the pivot occlusal portion. Optionally, a sleeve may further comprise filling material disposed between the pivot occlusal portion and the reinforcing sleeve.

Optionally other abutment structure may for example include but is not limited to a mold formed on the adjustable post, configured for mounting the prosthodontic restoration thereon.

Optionally and preferably, the abutment assembly may further comprise an interface member configured for adapting and/or interfacing between the implant anchor and abutment pivot. Optionally interface member may comprise an anti rotational interface for interfacing a corresponding anti-rotational interface provided on the implant anchor. Optionally and preferably the interface member can further include a cone portion for engaging a corresponding cone portion on the pivot mounting portion of the abutment pivot.

Unless otherwise defined, all technical and scientific terms used herein have the same meaning as commonly understood by one of ordinary skill in the art to which this invention belongs. The materials, methods, and examples provided herein are illustrative only and not intended to be limiting.

Importantly, this Summary may not be reflective of or correlate to the inventions protected by the claims in this or continuation/divisional applications hereof. Even where this Summary is reflective of or correlates to the inventions protected by the claims hereof, this Summary may not be exhaustive of the scope of the present inventions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 3A-D show various perspective views of a schematic illustration of an optional abutment pivot comprising a plurality of interlinked members according to an optional embodiment of the present invention;

FIGS. 4A-C show varied perspective views of a schematic illustration of an optional abutment pivot comprising a ball and socket joint, according to an optional embodiment of the present invention;

FIG. 7A is a side view of a an optional interface member according to an optional embodiment of the present invention;

FIG. 7B is a side perspective view an optional as depicted in FIG. 7A, according to an optional embodiment of the present invention;

FIGS. 8A-F shows various perspective views of a schematic illustration of optional interface members according to optional embodiments of the present invention;

FIGS. 9A-C show various views of a schematic illustration of optional sleeves according to optional embodiments of the present invention.

FIGS. 11A-C show various views of a schematic illustration of optional sleeve members, comprising a rim portion, according to an optional embodiment of the present invention;

FIGS. 12A-D show various views of a schematic illustration of optional locking nut member according to an optional embodiment of the present invention, FIGS. 12A-B showing a long locking nut member and FIGS. 12C-D showing a short locking nut member;

DETAILED DESCRIPTION OF EMBODIMENTS

Figure 1:
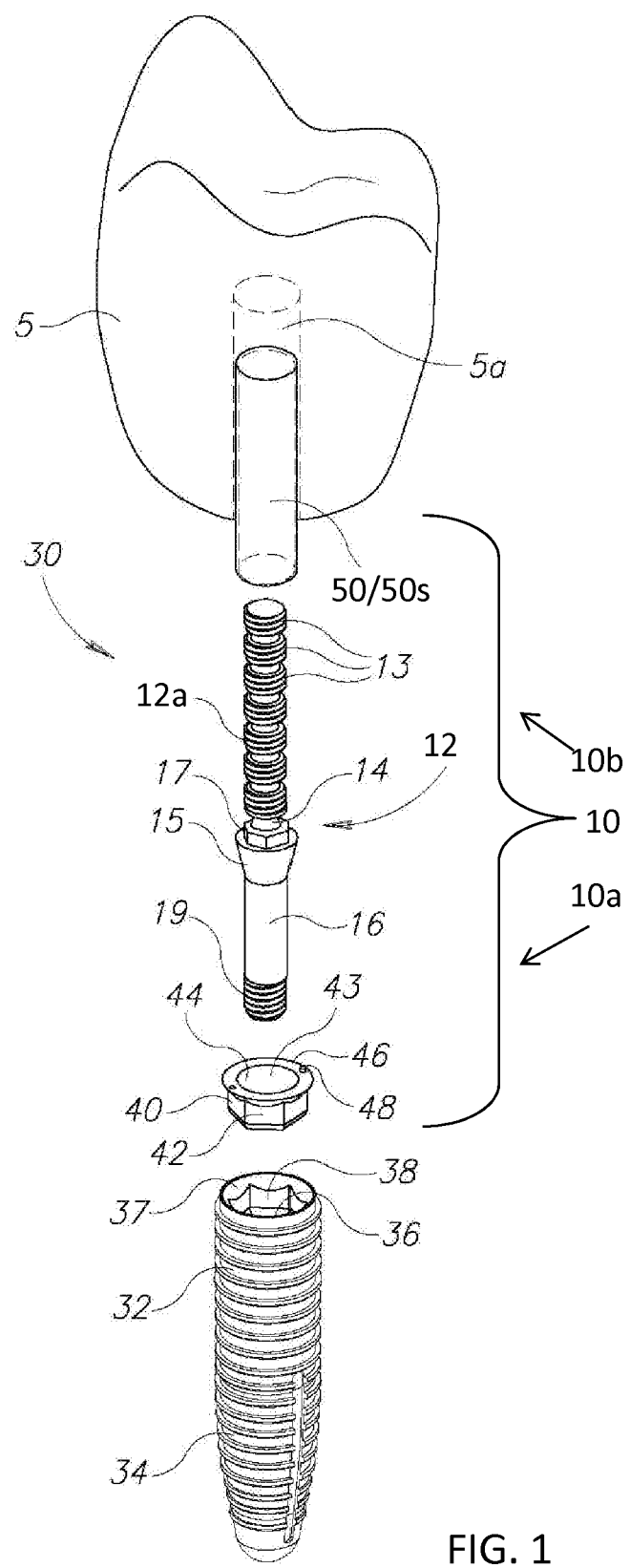
FIG. 1 is an exploded view of a dental implant system comprising an adjustable abutment assembly according to an optional embodiment of the present invention.

The principles and operation of the present invention may be better understood with reference to the drawings and the accompanying description. The following figure reference labels are used throughout the description to refer to similarly functioning components are used throughout the specification hereinbelow.

5 prosthodontic restoration;
5a mounting bore;
10 abutment assembly;
10a abutment assembly apical end;
10b abutment assembly occlusal end;
12 abutment pivot;
12a pivot projection/pivot occlusal portion;
12c pivot coupling member;
12e pivot extension member;
13 engageable portion;
13a first engageable portion;
14 adjustment portion;
14a first adjustment portion;
14i adjustable interlocking members;
14f female interlocking member;
14m male interlocking member;
15 stabilizing portion;
16 pivot mounting member/portion;
16s snap fit couplings;
17 screw head interface;
18 screw thread;
19 screw thread;
20 a first angle;
22 a second angle;
30 dental implant system;
32 conventional implant anchor;
33 screw thread;
34 screw thread;
36 anchor bore;
37 opening;
38 a hexagonal interface;
40 interface member;
40a interface member apical end;
40b interface member occlusal end;
42 hexagonal portion;
43 through-going aperture;
44 cone portion;
46 flange;
46a flange;
47 elevated rim portion;
48 protrusion;
49 transgingival portion (collar);
50 sleeve;
50a sleeve apical end;
50b sleeve occlusal end;
50c sleeve lumen;
50r rimmed sleeve;
50s sleeve assembly;
52 inner sleeve member;
52b rimmed inner sleeve;
52c coupling portion;
52d anti-rotational recess
52r inner sleeve recess;
52s sleeve inclination/slope
52t inner sleeve threading;
53 sleeve rim portion
54 outer sleeve member;
54b rimmed outer sleeve;
54e outer sleeve external surface;
54L pegs
54s outer sleeve internal surface;
55 jawbone;
56 residual teeth;
68 threaded stabilizing portion;
70 locking nut;
70a locking nut apical end, abutment end
70c locking nut external surface;
70r locking nut restoration end;
72 locking nut plug;
80a, 80b and 80c ball and socket abutment pivot;
82 adjustable pivot occlusal portion
90a, 90b and 90c ball joint arrangement
92a-c ball
94a-c seat
95 extension.

FIG. 1 is an exploded view of a full dental implant system 30 comprising an implant anchor 32, prosthodontic restoration 5 and an abutment assembly 10 according to an optional embodiment of the present invention. Most preferably state of the art implant anchors 32 is provided to replace the native tooth root (apical end), while abutment 10 and restoration 5 provide to replace the coronary portion of the tooth (occlusal end). Restoration 5 may be provided in the form of state of the art restoration and/or crowns made of materials as is known and accepted in the art, for example acrylics, porcelain, metals, alloys, glass cement, composites, resins, or the like.

Most preferably embodiments of the present invention provide for abutment assembly 10 with which restoration 5 may be associated about its occlusal end 10b, while implant anchor 32 may be associated about the apical end 10a, for example as shown.

Most preferably abutment assembly 10 may be formed from variable combinations of members including abutment pivot 12 (also depicted in FIGS. 2-5) having a pivot mounting member/portion 16 (FIGS. 6A-C) and occlusal portion 12a, that form the core of abutment assembly 10. Most preferably abutment assembly further comprises, at least one or more members selected from the group consisting of a sleeve 50, sleeve assembly 50s, inner sleeve member 52, outer sleeve member 54, (also depicted in FIGS. 9-11), composite buildup about pivot occlusal portion 12a (not shown), an interface member 40 (also depicted in FIGS. 7-8), and a locking nut member 70 (also depicted in FIGS. 12A-D) and locking member plug 72 (not shown).

Optionally the abutment assembly 10, any portion thereof, or any member thereof for example including but not limited to abutment pivot 12, pivot projection/occlusal portion 12a, sleeve 50, sleeve assembly 50s members, interface member 40, locking nut 70, locking member plug 72, may be provided with an opaque pigmentation layer for example a color and/or sealant and/or varnish and/or paint or the like covering and/or layering material so as to render abutment assembly 10 and/or members thereof aesthetically pleasing by concealing it, rendering it not visible for aesthetic purposes.

Most preferably pivot 12 forms the core of abutment assembly 10. Most preferably pivot 12 comprises an integral pivot mounting member 16 about its apical portion, and is fluidly and integrally formed therewith, such that most preferably pivot mounting member 16 and pivot 12 form a single unit. Optionally and preferably pivot mounting member 16 and pivot 12 are continuous with one another. Most preferably pivot mounting member 16 and pivot 12 are fabricated from the same materials as a single unit.

Most preferably pivot mounting member 16 provides for coupling and/or otherwise associating and/or facilitates the association and/or interfacing between abutment assembly 10 and anchor 32.

Optionally pivot mounting member 16 and pivot 12 may be provided from two individual members that may be coupled and/or associated with one another.

As will be described and shown in more details herein below, most preferably abutment 10 may be adjusted and positioned according to at least one or more prosthodontic parameters to ensure alignment of abutment 10 relative to residual teeth and/or other abutments on the same and opposite jaw.

Most preferably abutment assembly 10 may be adjusted, about at least one or more of its members, most preferably including but not limited to at least one of pivot 12 and/or interface member 40. For example, pivot 12 may be adjusted about its occlusal portion 12a so as to obtain any position to ensure alignment relative to residual teeth and/or abutments on the same and opposite jaw.

FIG. 1 shows abutment assembly 10 that may be mounted on a conventional implant anchor 32, having a screw thread 34 defined on its outer surface for screwing into the bone, for example as is known in the art. Anchor 32 defines a bore 36 having an upwardly facing opening 37 for insertion of an abutment therein. Opening 37 includes an anti rotational geometry, here illustrated as a hexagonal interface 38, which can be designed for engaging a corresponding interface defined on the abutment assembly for example including but not limited to interface member 40, thus horizontal rotation of abutment 10 may be precluded. According to an optional embodiment of pivot mounting member 16 of abutment pivot 12 may be provided without such a corresponding interface. Thus, in order to provide for mounting abutment assembly 10 via pivot 12 inside a conventional implant anchor, such as anchor 32, an interface member 40 may be provided, most preferably for adapting between the abutment assembly 10 and the anchor 32.

Optionally, interface member 40 may be formed as a ring-shaped member having a through-going aperture 43, configured for receiving pivot mounting member 16 of abutment pivot 12, when mounting member 16 is inserted into bore 36 of implant anchor 32.

Optionally and preferably, interface member 40 may be configured for adapting between the pivot mounting member 16 of abutment assembly 10 of the presently disclosed subject matter and any state of the art anchor 32. Thus, abutment assembly 10 may be used with any known anchor.

Optionally and preferably abutment assembly 10 comprises sleeve 50 and/or sleeve assembly 50s to facilitate interfacing and/or coupling and/or otherwise associating with restoration 5.

Figures 2A, 2B:
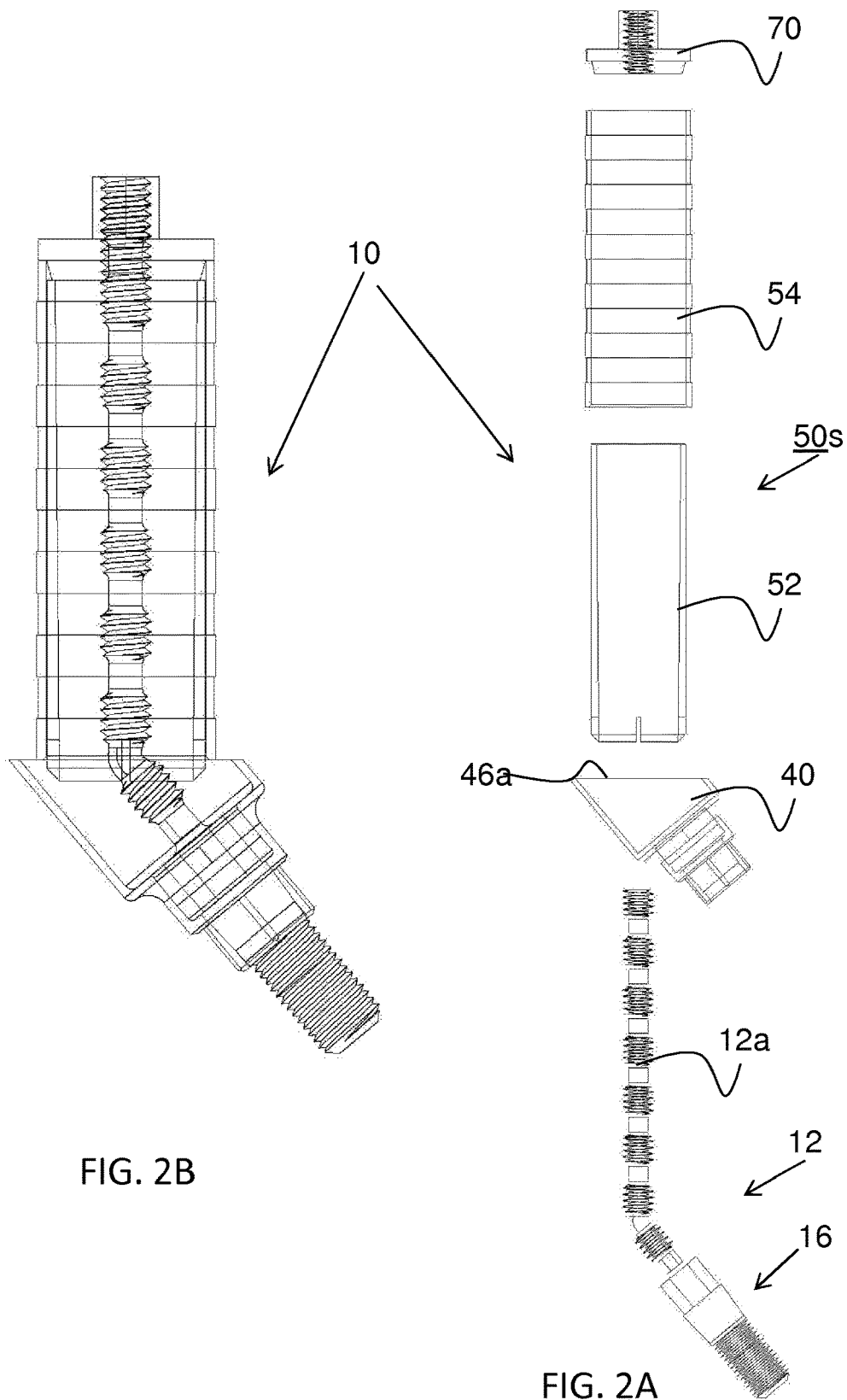
FIG. 2A is an exploded view of an abutment assembly according to an optional embodiment of the present invention.
FIG. 2B is an assembled view of the exploded view depicted of FIG. 2A showing an abutment assembly according to an optional embodiment of the present invention.

FIG. 2A shows an exploded view of an optional abutment assembly 10 comprising, abutment pivot 12 with an integrated pivot mounting member 16, interface member 40, sleeve assembly 50s comprising an inner sleeve 52 and an outer sleeve 54, and locking nut 70. FIG. 2B shows an assembled view of exploded view depicted in FIG. 2A showing an assembled abutment 10 comprising an adjusted abutment pivot 12 and interface member 40. As shown at least one or more portions and/or members comprising abutment 10 may be adjusted according to at least one or more prosthodontic parameters. For example, pivot 12 may be adjusted so as to obtain any position to ensure alignment relative to residual teeth and/or abutments on the same and opposite jaw. Optionally, interface member 40 may be adjusted, sized and/or contoured, for example as shown defining a flange 46a. Most preferably interface member 40 is adjusted with respect to the gingival tissue and in relation to pivot 12 to provide abutment 10, with the correct position and shape while conforming to the prosthodontic requirements. Most preferably the proper direction and geometry of abutment assembly 10 ensures that a restoration 5 is provided with proper alignment relative to residual teeth and/or abutments on the same and opposite jaw.

Optionally and most preferably interface member 40 is adjusted such that it is apically reduced by cutting and/or filing in relation to with the alveolar bone, the gingival, and is substantially perpendicular with respect to the adjusted abutment pivot 12 and substantially parallel to the occlusal plane.

As shown abutment assembly 10 is most preferably centered and/or built around pivot 12, therein pivot 12 provides for receiving and/or associating with interface member 40, sleeve members 52, 54, and locking nut 70 essentially in a concentric manner.

Figures 2C, 2D:
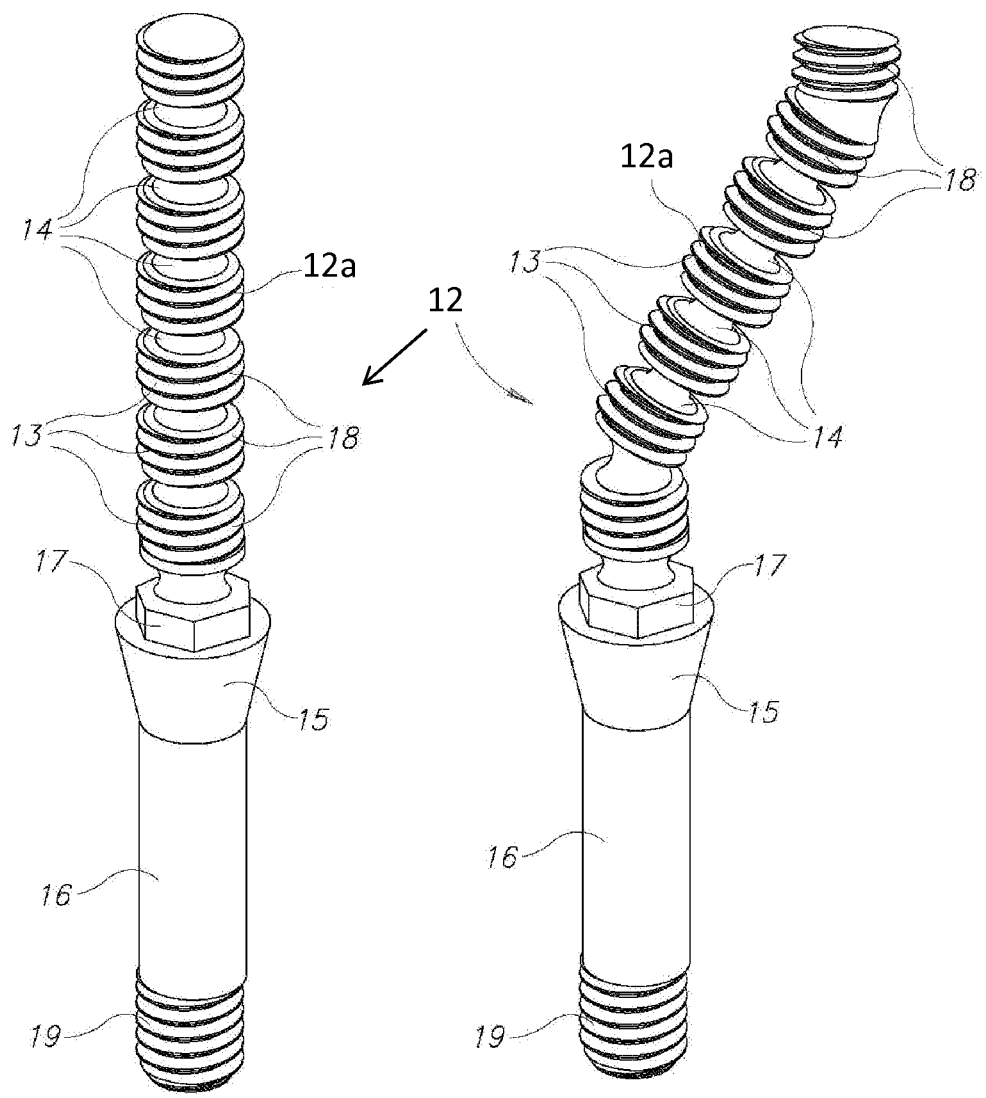
FIGS. 2C-E show various perspective views of an abutment pivot according to an optional embodiment of the present invention.

FIGS. 2C and 2D illustrate and optional embodiment of pivot 12 and pivot mounting member 16 form the core of abutment assembly 10. FIG. 2C shows pivot 12 in a straight position and/or unadjusted position, while FIG. 2D shows pivot 12 following an adjustment wherein pivot 12 is positioned and shaped according to the required angle, direction and form due to the prosthodontic requirement and individual morphology. Abutment assembly 10 includes a pivot occlusal portion 12a for affixing a prosthodontic restoration thereto, and a pivot mounting member 16 for mounting on an implant anchor 32.

Pivot 12 is most preferably adjustable about the pivot occlusal portion 12a and may be made of a shape-retaining material having a certain degree of plasticity, allowing a practitioner to manipulate its shape, length, angle and direction with respect to pivot mounting member 16 and/or anchor 32, so as to achieve adequate alignment of abutment assembly 10 with respect to other abutments and/or with respect to other teeth in the patient's mouth.

Pivot 12 may optionally be made of metal, such as titanium, titanium alloy, tantalum, tantalum alloy, zirconium, or plastic and thermo plastic, carbon fiber, fiberglass, antibacterial metals, the like, any combination thereof, or any other appropriate material and/or biocompatible material.

Optionally and preferably the diameter and shape of pivot 12 may be selected in such a way so as to allow adjustment thereof while preserving the implant structures and perio-implant tissue.

Most preferably, pivot 12 may be adjusted as desired in any angle and any horizontal and/or vertical direction, so as to achieve substantial parallelism and inter-occlusal alignment between abutments and/or teeth of the same or opposite jaws. In addition, the length of pivot 12 may be adjusted about occlusal portion 12a by cutting thereof and/or extending pivot 12 with a pivot extension member 12e (described in FIGS. 5A-D). Most preferably adjustment of pivot length may be provided so as to achieve the optimal length of abutment assembly 10 with respect to the residual teeth and/or abutments on the same and opposite jaw. Optionally and preferably adjustment of the length of pivot 12 may be provided so as to account for the thickness of restoration 5 about its occlusal surface, which in turn ensures the durability of restoration 5 as well as other prosthodontic requirements associated with restoration 5.

Optionally and preferably, pivot 12 comprises at least one and most preferably a plurality of engageable portion 13 for affixing thereto, additional structures, for example including but not limited to prosthodontic attachments, prosthodontic restoration 5, an abutment structure, or the like. Optionally engageable portion 13 may facilitate coupling and/or association with members of abutment assembly 10 either directly (without composite material) or indirectly (with composite material) for example including but not limited to interface member 40, sleeve 50, sleeve assembly 50s, pivot extension member 12e, locking nut 70, plug 72, prosthodontic restoration 5, prosthodontic attachments, composite materials, or the like in any combination thereof.

Optionally and preferably, portion 13 may optionally be provided in the form of threading, for example in the form of screw thread 18 defined about pivot occlusal portion 12a (FIG. 2E), for facilitating associating with and/or coupling and/or affixing additional structures onto pivot 12.

Optionally portion 13 may be provided with a textured surface for example consisting of grooves and/or ridges, or similar texture, having increased surface area, or the like shape or form.

Optionally and preferably pivot 12 may be provided with markings along its length. Wherein pivot 12 is marked at several locations along its length in order to indicate to practitioner the length from a predetermined reference point, the adequate adjustment level, available angle of adjustment, optional adjustments at a particular marking point, or the like physical and/or mechanical parameter and/or visual indicator. Optionally and preferably marking along pivot 12 may be provided on and/or define an adjustment portion 14 and/or engageable portion 13.

Optionally markings along pivot 12 may be disposed about pivot mounting member 16.

Most preferably pivot 12 comprises a plurality of indicator portions defined along the length thereof that provide and define an adjustment portion 14. Most preferably adjustment portion 14 may be provided so as to provide a controllable adjustment point along pivot 12. Most preferably adjustment portion 14 may provide and maintain the overall material composition, structure, and strength of the pivot material while pivot 12 is adjusted. Optionally and most preferably portion 14 provides for controlling the customization, adjustment, shape and length of pivot 12.

Optionally adjustment portion 14 may be provided between engageable portion 13.

Most preferably adjustment portion 14 may be provided with a radius. Optionally the radius may be provided as function of the diameter and the material characteristics of pivot 12. Most preferably the radius of adjustment portion 14 provides for maintaining the structural integrity and strength of pivot 12.

Optionally and preferably adjustment portion 14 provides a plurality of adjustment points providing a practitioner to both adhere to the prosthodontic requirements and material strength of the abutment avoiding sheer stress of pivot 12.

Optionally pivot 12 may be adjusted in more than one location along its length thereof, in the same direction or in a different direction, for example, for achieving a spatial structure. Optionally and preferably pivot 12 may be adjusted about an adjustment portion 14.

Adjustment portion 14 is most preferably configured and designed to facilitate customizing, shaping and adjusting pivot 12 to a desired shape, length, form, angle and direction. Optionally, adjustment portions 14 may be utilized for engaging a filing material, such as used for mounting a sleeve 50 on the pivot 12, or for forming a build up for example made of composite materials.

Optionally and preferably pivot 12 may be provided with a plurality of optional engageable portions 13 and adjustment portions 14. Optionally and preferably the relative size and distribution of engageable portion 13 and adjustment portion 14 along the length of pivot 12 may vary and may be provided in any manner. For example, the relative locations of portion 13 and adjustment portion 14 may be provided according to a fixed ratio. Optionally the ratio between portion 13 and adjustment portion 14 may be provided according to prosthodontic requirements.

Optionally, the adjustment portion 14 may be provided with a constant preset length while the engageable portion 13 may be provided with variable changing lengths. Optionally, both portion 13 and 14 may be provided with a preset and/or constant lengths along the length of pivot 12. Optionally, portion 13 may be set while adjustment portion 14 may be variable.

Optionally the ratio of portions 13 to portion 14 may be about 1.0 mm of engageable portion 13 to 1.0 mm of adjustment portion 14. Most preferably engageable portion 13 is provided with a uniform and/or continuous engageable members for example including but not limited to threading, that is continuous along the length of pivot 12, therein ensuring the continuity of engageable portion and/or threading 13/18 along pivot 12.

Figure 2E:
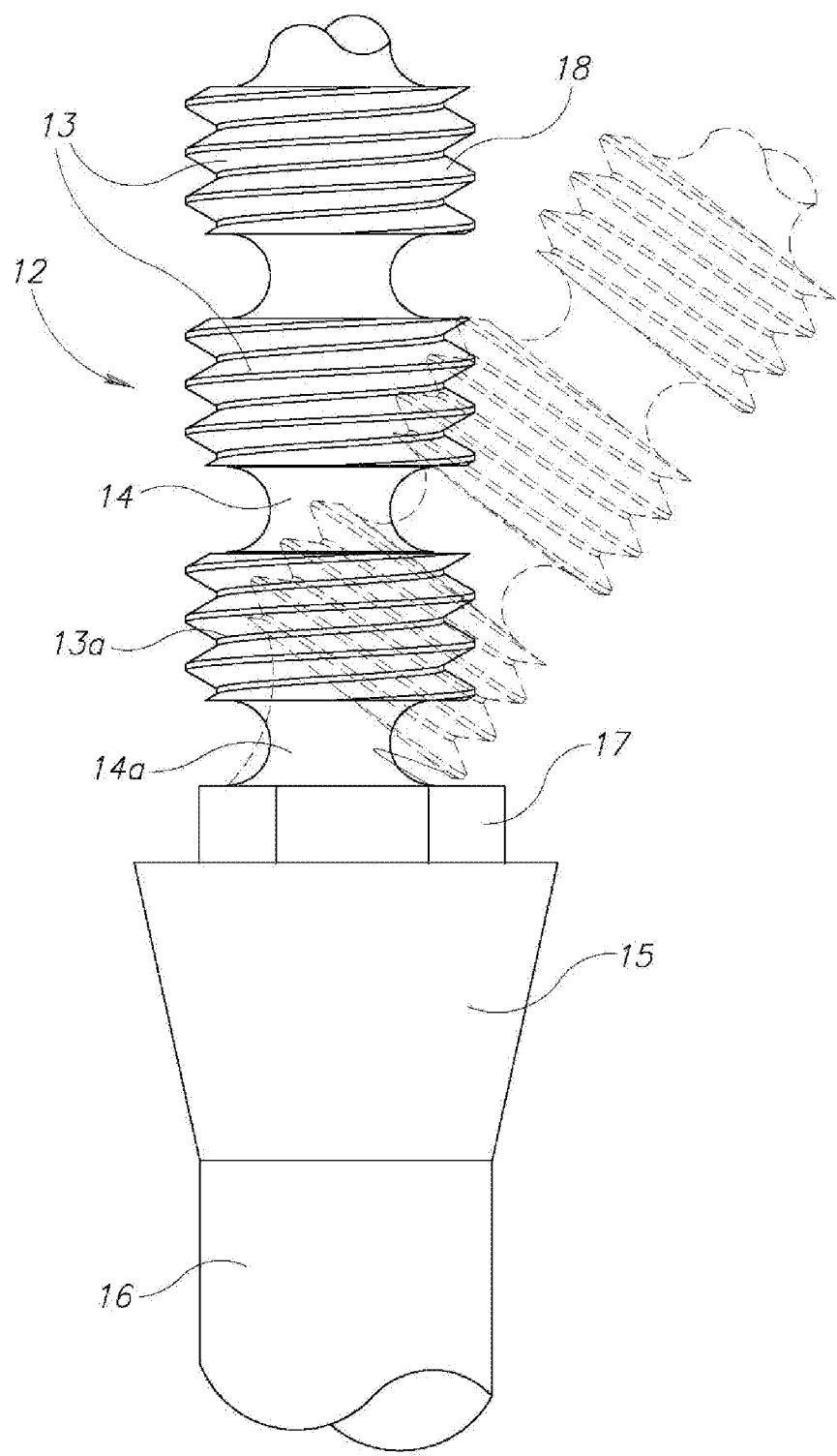

As best seen in FIG. 2E, when preparing the abutment, for example by a dentist or a dental technician, pivot 12 may be adjusted with respect to the axis of anchor 32, providing pivot 12 with the required prosthodontic position, adjusted about portion 14. Optionally, pivot 12 may be further adjusted to control the height and/or length of abutment 10, in relation to the inter-occlusal plan determining the vertical dimension.

It will be appreciated that the shape including, but not limited to, the length and/or thickness, of each engageable portion 13 may be determined at least partially in accordance with the maximum tilting angle required. This may be due to the fact that the engageable portion, for example first engageable portion 13a and first adjustment portion 14a (as shown in FIG. 2E), which are disposed in close proximity to interface 17, may limit the adjustment of the pivot 12, by abutting interface 17, when the pivot 12 is adjusted. Accordingly, each engageable portion 13 and/or adjustment portion 14 defined along pivot 12 may have a different shape, which may be determined in accordance with the maximum adjustment angle required about its location.

Optionally, the diameter of the pivot 12 may be different in different location along the length thereof, therein providing variable elasticity and plasticity along its length that in turn allows for controlling the adjustment of pivot 12 at each location. For example, the occlusal portion 12a of Pivot 12 may have a substantially smaller diameter than the diameter of the lower portion of pivot 12. This optional configuration provides for maintaining the elastic properties of pivot 12 while it is manipulated. For example, when a practitioner manipulates pivot 12 about its upper portion in order to adjust the angle and direction of pivot 12, the manipulation is performed while maintaining the elastic properties of pivot 12 and without compromising the material strength and staying within the limits of the tensile strength of the material, and prior to changing its structural composition from elastic phase to plastic phase.

Optionally, pivot 12 may be provided in a plurality of optional shapes and/or profiles for example including but not limited to, elliptical, cylindrical, oval, polygonal of n sides (where n is at least 3 or more), or any geometric shape.

Optionally occlusal portion 12a may be provided with oval shape, therein defining an oval pivot, that may be utilized when restoring a dental implant in a narrow space. An optional oval pivot may be disposed with its two opposite narrow portions facing the facial and oral cavity, respectively, and the two opposing wide portions disposed facing the adjacent abutments or teeth.

Optionally pivot 12 may be of any straight edge shapes and/or profiles such as, triangular, rectangular, polygonal having n sides (wherein n is at least 3) or the like geometric shape. For example, a triangular pivot may be configured to have a base thereof that may be vertically facing the oral cavity and its opposite corner may be facing facially. Optionally a triangular pivot may be particularly useful in narrow spaces for example, when the space between the teeth and/or abutments is substantially narrow.

Optionally the occlusal portion 12a of pivot 12 may be provided in the form of a spring (not shown), for example a shape retaining spring.

FIGS. 3A-D shows variable views of a schematic illustration of an optional pivot 12 formed from a plurality of adjustable interlocking members 14i, comprising a male portion 14m and a female portion 14f, formed about the occlusal portion 12a of pivot 12. Most preferably interlocking members 14i may be maneuvered relative to one another and/or to the axis of anchor 32, so as to assume a plurality of angles, profiles or configurations. Optionally and preferably the relative position of interlocking member 14i may be set and/or locked and/or fixed into position once they are set.

FIG. 3A shows pivot 12 provided from a plurality of interlocking members 14m and 14f, that may be maneuvered relative to one another, for example including but not limited to link members, maneuverable male-female joints or couplings, snap fit members, ball and socket formations, interlocking semispherical and/or semicircular members with corresponding socket, or the like. Most preferably interlocking member 14i may form any shape, plurality of angles, profiles or configurations for example as shown in FIG. 3C.

Optionally pivot 12 of FIGS. 3A-D may comprise a central lumen adapted for receiving a stylet, malleable rod, or the like locking member (not shown) for setting, maintaining, fixing and/or locking the interlocking members 14i relative to one another, therein fixing and/or maintain the adapted shape of pivot 12. Optionally and preferably such a locking member may be provided from optional materials that may be malleable and/or capable retaining various shape configuration corresponding to the shape of the central lumen assumed by pivot 12 of FIGS. 3A-D. Optionally the locking member (not shown) may be provided from various materials for example including but is not limited to fiberglass, nitinol, polymers, composite, any combination thereof or the like.

Figure 4C:
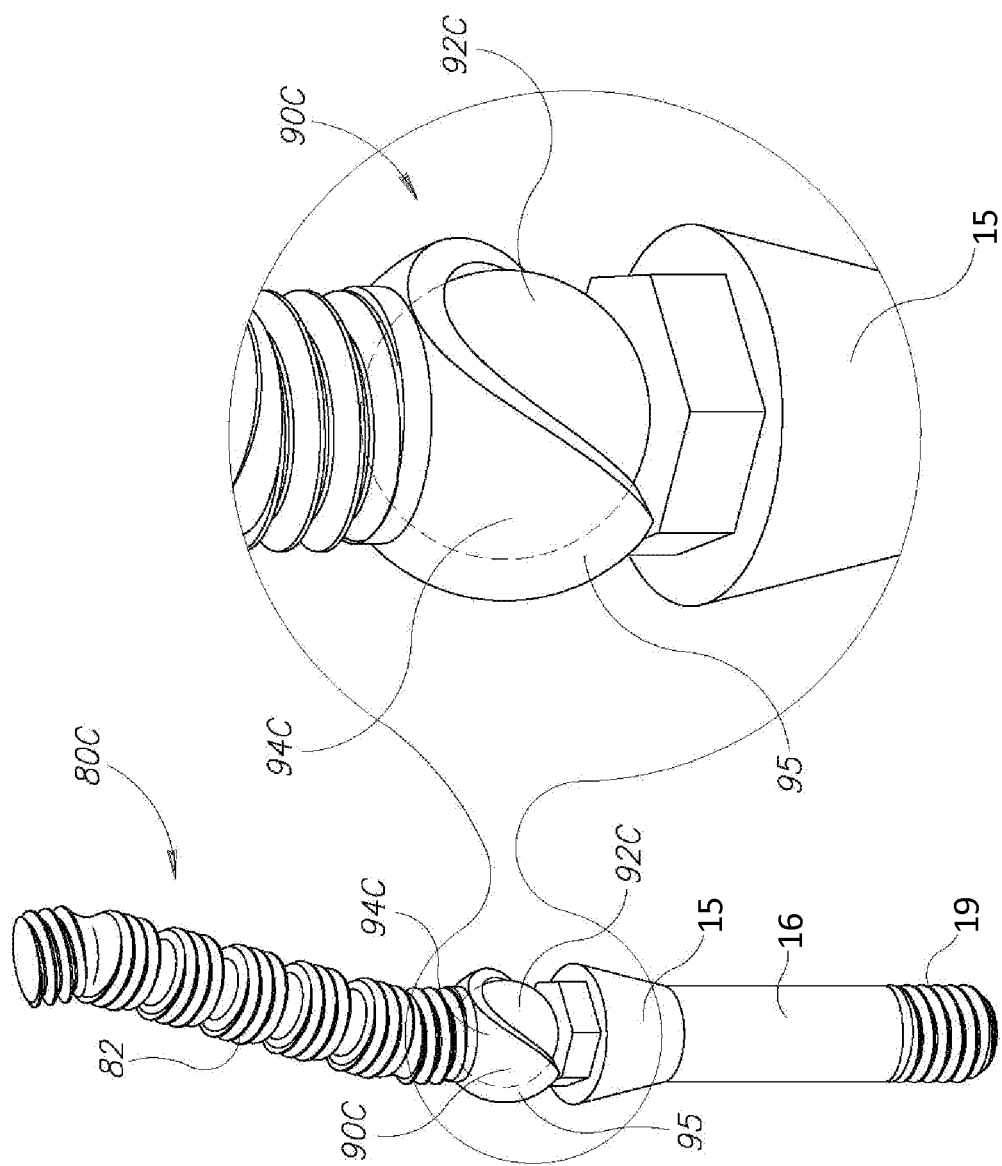

Referring now to FIGS. 4A-4C, showing an optional ball and socket abutment pivot arrangement according an optional embodiment of the present invention. FIGS. 4A-C shows ball and socket abutment pivot an 80a, 80b and 80c. Ball and socket abutment pivot 80a, 80b and 80c are substantially similar to abutment pivot 12 as previously described in FIGS. 2C-E, and include an adjustable pivot occlusal portion 82 having at least one or more engageable portions 13. Pivots 80a, 80b, 80c further comprise pivot mounting member 16 having threading 19 for coupling to a corresponding screw thread 33 disposed inside a bore 36 of an implant anchor 32, and a stabilizing portion 15. Most preferably, ball and socket abutment pivot 80a, 80b and 80c, comprise a ball joint arrangement 90a, 90b and 90c respectively, for manipulating the adjustment of the abutment pivot 80a, 80b, 80c about portion 82.

FIG. 4A shows ball joint arrangement 90a of pivot 80a disposed between the apical end of pivot adjustable portion 82 and stabilizing portion 15, as shown. Most preferably ball joint arrangement 90a includes a ball member 92a mounted at the apical end of adjustable pivot occlusal portion 82 with the corresponding seat 94a provided about the stabilizing portion 15. Most preferably ball 92a may be configured to be snugly fit inside a seat 94a coupled to the top portion of pivot mounting member 16. Optionally and preferably seat 94a comprises at least one or more recess to provide the elasticity required for retentively receiving ball 92a. Seat 94a may be configured to allow ball 92a to rotate therein in any direction along the occlusal plane and/or any angle relative to the pivot mounting member 16 and/or anchor 32, thus allowing swiveling of post 82 in any desired direction and/or angle.

Optionally and preferably, adjustable pivot occlusal portion 82 may be further manipulated and/or adjusted about portion 82 in at least one or more location along its length.

Optionally and preferably in order to retain ball 92a inside seat 94a, the latter may be provided with a narrow portion (not shown), having a diameter which is substantially smaller than the diameter of ball 92a, thus ball 92a is retained inside seat 94a by the narrow portion. Optionally, any other suitable retaining means may be utilized.

The ball joint arrangement 90b illustrated in FIG. 4B comprises a ball 92b mounted about the occlusal end of mounting member 16, adjacent to stabilizing portion 15, as shown. Ball 92b is configured to be snugly fitted inside a seat 94b which according to this example is coupled to the apical end of adjustable post 82, as shown. Retaining ball 92b inside seat 94b may be carried out in a fashion as described in regards to FIG. 4A, or in any other suitable fashion. Optionally and preferably seat 94b comprises at least one or more recess to provide the elasticity required for retentively receiving ball 92b.

The ball joint arrangement 90c illustrated in FIG. 4C, is substantially the same as the ball arrangement of FIG. 4B, however further comprising extension 95 provided to limit the tilting and maneuverability of ball the joint. Ball join 90c includes a ball 92c defined at the occlusal end portion of mounting member 16 adjacent to stabilizing portion 15 and a seat 94c is coupled to the apical end of adjustable post 82, as shown. Seat 94c includes an extension 95 on one side thereof, provided to limit the tilting of adjustable pivot occlusal portion 82 relative to mounting member 16 and/or anchor 32. Most preferably extension 95 is configured to engage mounting member 16, therein delimiting the tilting thereof toward the side of extension 95. This way, adjustable pivot occlusal portion 82 cannot be tilted toward the side of extension 95. Extension 95 may include more than one side, thus precluding tilting of post 82 toward more than one side. In fact, extension 95 may be configured to encase the entire circumference of ball 92c, apart from one portion or a groove, thus allowing post 82 to be tilted only about Optionally and preferably seat 94c comprises at least one or more recess to provide the elasticity required for retentively receiving ball 92c.

Optionally ball 92 and seat 94 may be fixed in position between post 82 and mounting member 86 with a locking nut for example nut 70 as previously shown. Most preferably the circumference of ball 92 is configured to be slightly larger than the circumference of seat 94 disposed about adjustable pivot occlusal portion 82. For example, nut 70 may be threaded over adjustable pivot occlusal portion 82 to lock and fix ball 92 within seat 94. Most preferably adjustable pivot occlusal portion 82 may be provided with a ball joint recess adjacent to seat 94, wherein a locking member, for example locking nut 70, provides for closing the ball joint recess about seat 94 over ball 92. Most preferably locking member may have a slightly larger circumference than seat 94, therein fixing and/or setting the position of ball 92 within seat 94 to maintain the direction and angle of occlusal portion 82.

Optionally pivot 12 may be extended with a plurality of optional internal and/or external coupling members for example including but not limited to threading, snap fit, pressure fit, male to female couplers, or the like coupling members.

Optionally the height and/or length of pivot 12 and therein abutment assembly 10 may be controlled either by reducing its size or by lengthening with an optional pivot extending member 12e, depicted in FIGS. 5A-D. Optionally pivot 12 may be provided with a standard size, and sized according to patient parameters for example including the individual's morphology and related prosthodontic requirements. Optionally pivot 12 may be provided in short form or long form, as shown in FIGS. 2C-D.

Optionally and preferably adjusting abutment 10 further provides for substantially achieving parallel alignment with other abutments or with residual teeth.

Optionally and preferably adjusting pivot 12 may be provided with conventional tools or with dedicated tools. Optionally and preferably, in order to achieve optimal alignment, dedicated alignment equipment may be utilized.

Figure 5D:
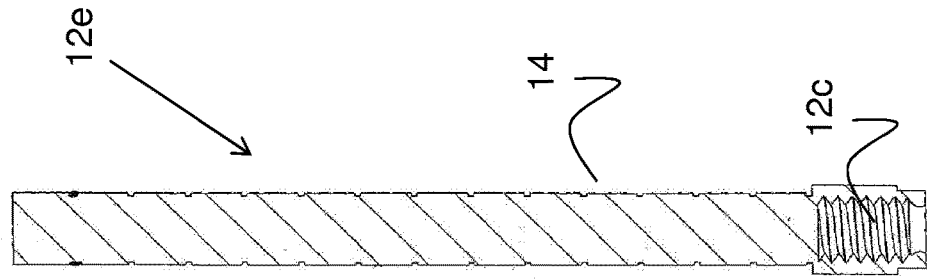
FIGS. 5A-D show varied views of a schematic illustration of optional abutment pivot extension member, according to an optional embodiment of the present invention.
Figure 5C:
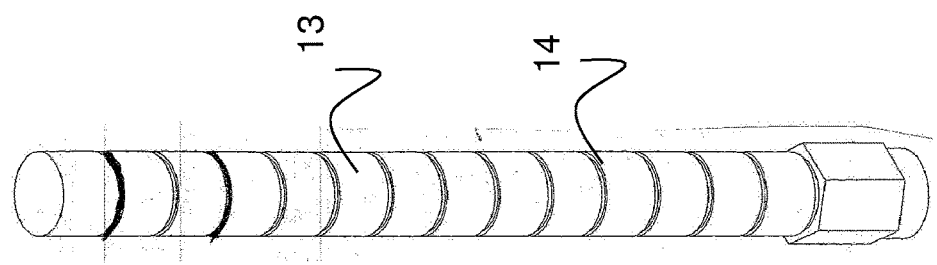
Figure 5B:
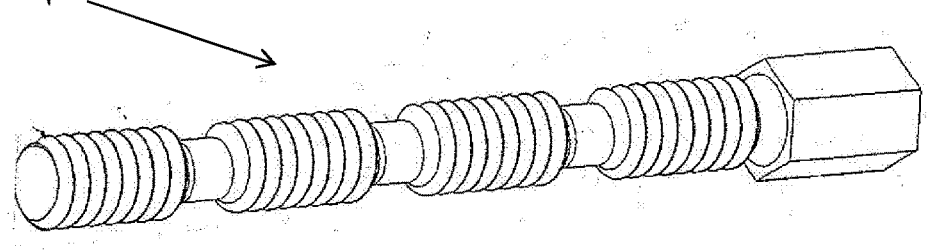
Figure 5A:
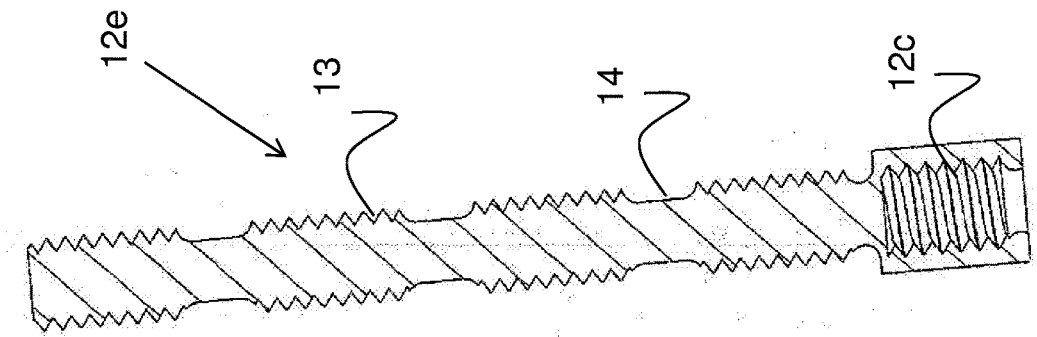

FIGS. 5A, 5C show cross sectional views of optional pivot extending members 12e, that may be utilized to extend or lengthen pivot 12 of abutment assembly 10. Optionally and most preferably pivot extending member 12e may be coupled with pivot 12 over coupling member 12c that may correspond to engageable portion 13, as shown in FIGS. 2C-E. Optionally coupling member 12c may be provided in optional forms for example including but not limited to male to female couplers, snaps, threading, pressure fit or the like.

FIGS. 5B, 5D show perspective views of pivot extending member 12e shown in FIGS. 5A-C, showing optional adjustment portion 14 and engageable portion 13. FIG. 5C shows an engageable portion 13 that does not comprise threading, while FIG. 5B shows engageable portion 13 fit with threading. FIG. 5B shows pivot extending member 12e having a larger adjustment portion 14, while FIG. 5D shows pivot extending member 12e having a small adjustment portion 14 relative to the respective engageable portion 13. Optionally pivot extension member 12e may be provided with a textured surface with a textured surface for example consisting of grooves and/or ridges, or similar texture, having increased surface area the like shape and/or form.

Pivot mounting member 16 most preferably provides the means by which pivot 12 is securely coupled or otherwise associated with an anchor 32. Most preferably pivot mounting member 16 may be configured to be inserted in bore 36 of an implant anchor 32 (for example as illustrated in FIG. 1). Optionally and preferably, at least a portion of pivot mounting member 16 may comprise threading along its length. For example threading 19 may be provided for coupling to corresponding threading 33 disposed inside bore 36 of an implant anchor 32 (FIG. 13), most preferably provided to couple and/or fasten abutment assembly 10 to implant anchor 32. Optionally threading disposed about the length of pivot mounting member 16 may be provided about any portion thereof for example threading 68 disposed about stabilizing portion 15 as shown in FIG. 6D. Optionally threading may be disposed about a plurality of portions about pivot mounting member 16. For example, pivot mounting member 16 may comprise threading 19 about its distal end as well as threading 68 about stabilizing portion 15.

Most preferably, pivot mounting member 16 comprises a stabilizing portion 15 providing additional stability when coupling pivot 12 and implant anchor 32. Most preferably stabilizing portion 15 provides for evenly transferring forces, such as masticatatory forces, and lingual and labial tension, applied on the prosthodontic restoration and transfers them to the jawbone through the anchor.

Optionally stabilizing portion 15 may be provided with optional profiles and/or shapes for example including but not limited to conic, cylindrical, or the like in any geometric configuration. Most preferably stabilizing portion 15 is provided with a conic profile, that may provide both stability and to lock pivot 12 with anchor 32.

Optionally, pivot mounting member 16 may further comprise an interface 17, that may be manipulated with a tool, therein optionally and preferably providing for manipulating pivot 12 relative to anchor 32. Optionally interface 17 may be provided in the form of a screw head interface 17, for example including but not limited to a hexagonal screw head portion, such as is illustrated herein, or the like screw head shape as is known in the art. Optionally interface 17 may be configured to be engaged by means of a tool, such as a wrench and/or the like or any dedicated tool, so as to allow for rotatable fastening abutment 10 to an implant anchor 32, for instance by rotating interface 17 that in turn screws threading 19 of pivot mounting member 16 to a corresponding screw thread defined inside the bore 36 of the implant anchor 32.

It will be appreciated that, alternatively, mounting abutment 10 to an implant anchor 32 may be carried out in any other fashion, for example by cementing, utilizing dental cements or adhesives or the like as is known in the dental art. Optionally abutment 10 may be coupled to anchor 32 via pivot mounting member 16 by way of friction fit, snap fit, press fit, or the like couplings.

Figure 6C:
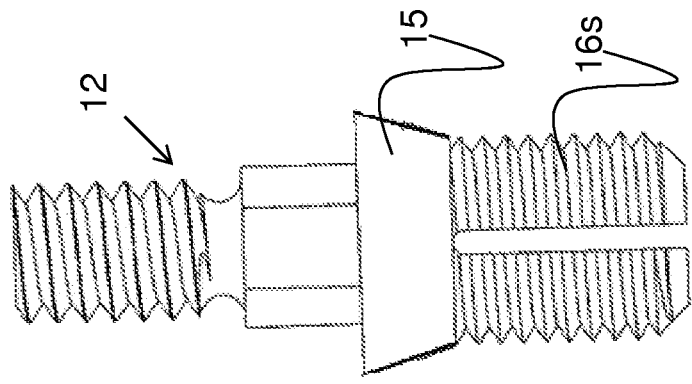
FIGS. 6A-D show schematic illustrations of a close up partial view of optional abutment pivot mounting member portions according to optional embodiments of the present invention.
Figure 6B:
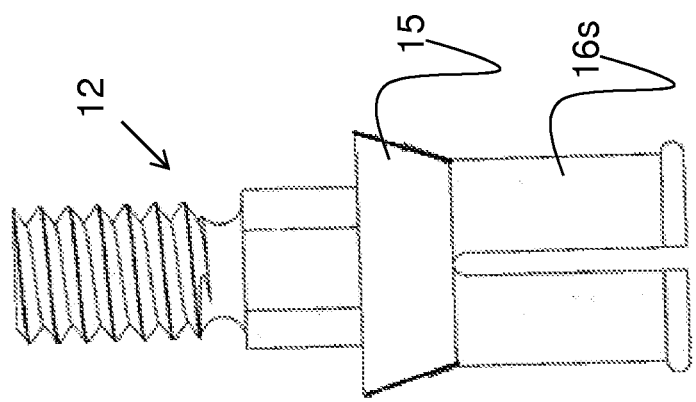
Figure 6A:
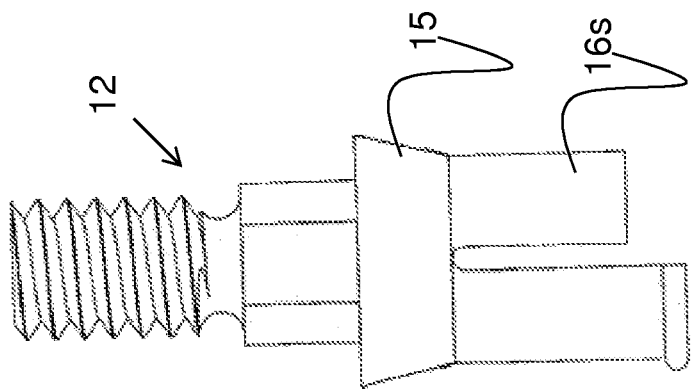
Figure 6D:
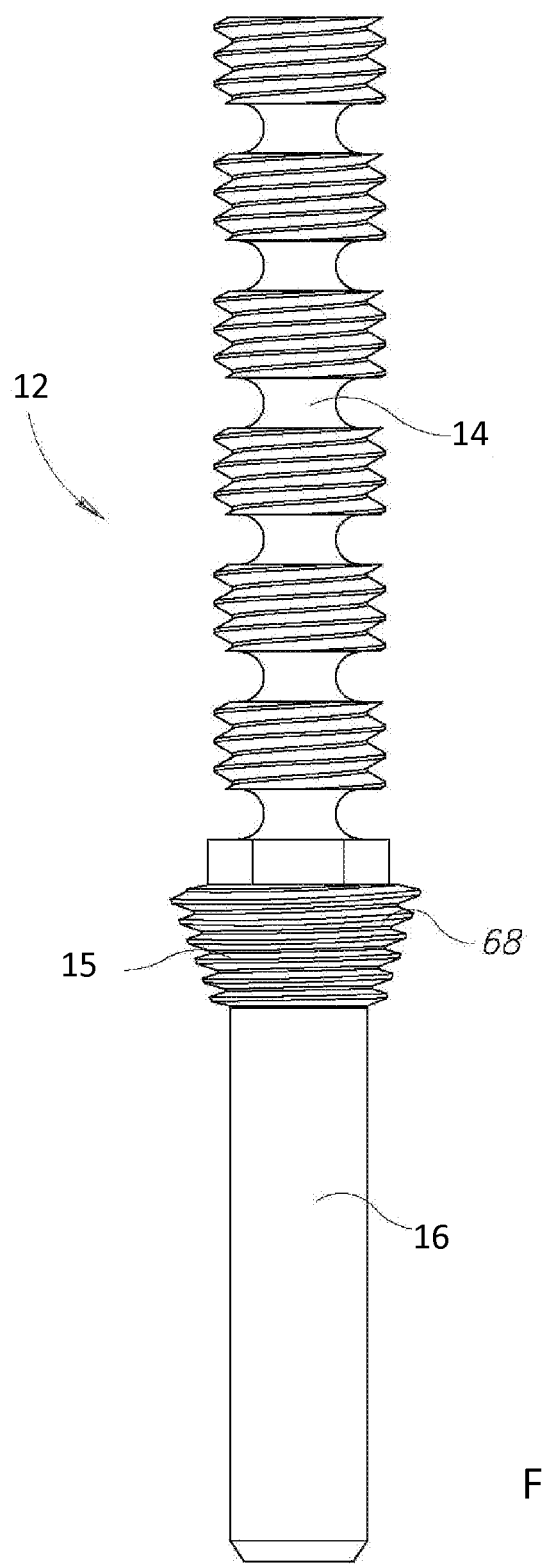

FIGS. 6A-C, shows optional snap fit couplings 16s that may fit within bore 36 of anchor 32. Optionally pivot mounting member 16 may provided with a conic and/or cylindrical profile having an angle of less than 2 degrees, otherwise known as a Morse taper and/or Morse angle, therein providing for friction fit and locking and/or securely fastening between bore 36 and pivot mounting member 16.

Optionally stabilizing portion 15 may be provided with conical threading 68 for example as shown in FIG. 6D. Threading 68 most preferably provides for securely fastening pivot 12 with anchor 32 and/or interface member 40. Most preferably pivot mounting member 16 may be coupled and/or fixed and/or otherwise associated with any implant anchors. Optionally if an implant anchor is not provided with a bore 36, any member of abutment 10 may be configured to be coupled externally with anchor 32.

For example, an anchor comprising a connective platform for example in the form of a protruding interface (not shown) having a portion with internal and/or external threading, such an anchor may be coupled with abutment pivot 12 via pivot mounting member 16 configured and provided with corresponding internal and/or external threading to couple with the anchor's protruding interface and/or the like coupling interface.

For example, an anchor comprising a protruding interface (not shown) for example a hexagonal interface, having a portion with internal and/or external threading may be coupled with abutment 10 via pivot extending member 12e that may be provided with a corresponding internal and/or external threading for coupling with an anchor's protruding interface.

For example, an anchor comprising a protruding interface (not shown) for example in the form of an external interface (also known as an external hex, hexagonal anti-rotational member) or the like anti-rotational means, as is known in the art, having a portion with internal threading about bore 36, may optionally and preferably be coupled with pivot 12 via interface member 40. Optionally and preferably interface member 40 may be provided with a corresponding anti-rotation member configuration, for example an internal hex, for associating with the external hex of the anchor, while pivot 12 may be threaded and securely coupled with the anchor about internal threading disposed about bore 36 to facilitate coupling pivot 12 with the anchor's protruding interface.

Now referring to FIGS. 7A and 7B, showing an optional interface member 40 comprising a portion 42 defined on its outer surface, corresponding to the hexagonal interface 38 of implant anchor 32. In addition, interface member 40 comprises a corresponding portion 44 defined on the inner surface of aperture 43, for engaging stabilizing portion 15 of pivot mounting member 16.

Optionally portion 42 may be provided in a plurality of shapes so as to fit with the interface of implant anchor 32. Portion 44 may be provided in a plurality of optional shapes so that inner surface 43 may fit with shape and/or profile of stabilizing portion 15. For example, portion 44 may be provided with a cylindrical profile about surface 43 to fit with a cylindrical stabilizing portion 15.

Interface member 40 comprises an apical end 40a and an occlusal end 40b. Most preferably apical end 40a provides for interfacing with anchor 32, while occlusal end provides for interfacing with prosthodontic attachments, restoration 5, sleeve 50, sleeve assembly 50s, 52, 54 and or filling material. Optionally the diameter of occlusal end 40b is at least equal to or larger than the diameter of apical end 40a. Optionally the diameter of apical end 40a may be provided relative to the size of anchor 32.

Interface member 40, according to one example, may further comprise a flange 46 disposed about the periphery thereof for engaging other portions and/or members of the abutment assembly 10 most preferably sleeve 50, sleeve assembly 50s, 52, 54, restoration 5, prosthodontic attachments or filling material.

It is appreciated that interface member 40 may be provided with various other interface designs for interfacing a complementary coupling interface and/or anti rotational interface provided on the implant anchor. For example, if the anti rotational geometry is an outer hexagonal interface defined about the outside periphery of opening 37, the interface member 40 may include a corresponding hexagonal interface defined about the inner periphery thereof. Similarly, if the anti rotational geometry provided in implant anchor 32 is in the form of triangular or rectangular surface, the interface member 40 may include corresponding surfaces, so as to serve as an adapter and to allow mounting the abutment assembly 10 members, in particular abutment pivot 12, on any conventional implant anchor 32.

As best seen in FIGS. 7A and 7B, an optional flange 46 may be provided with an upward protrusion 48 for engaging the filling material inside the sleeve 50. When the filling material is dry and sufficiently rigid, the protrusion 48 serves as a stop member and precludes the rotation of the sleeve and the filling material about pivot 12. It is appreciated that the protrusion 48 may be replaced with any other engaging element, for engaging the filling material inside the sleeve 50. In addition, cone portion 44 may be provided with inner grooves for temporarily engaging the pivot mounting member 16, so the latter does not rotate before the sleeve and filling material is disposed thereon.

Optionally and preferably interface member 40 may include an elevated rim portion 47, for example as shown in FIGS. 8A-F, where elevated rim 47 may be provided to allow perio-implant tissue to heal around the interface member 40, and for defining and customizing flange surface 46a facilitating formation of a finish line. Optionally the customization of rim 47 providing flange 46a with a plurality of optional cross-sectional profile, profile, shapes and/or contours for example including but not limited to circular, elliptical, oval, sinusoidal, or the like.

Most preferably, elevated rim 47 allows tissue around implant 30 to rest stably around and heal passively. Most preferably, abutment assembly 10 may then be coupled with and/or mounted within anchor 32, without having to perform multiple surgeries, without the use of a healing cup, and without having to perform multistage procedures when adjusting the abutments.

Optionally interface member 40 may be provided and or realized in the form of an adjustable and/or customizable healing cup that most preferably may be adjusted in substantially real time to provide a healing cup that is adjusted in accordance with the individual morphology of perio-implant tissue, during the implantation process. Optionally and preferably the interface member 40 may then be utilized in forming the abutment assembly 10 according to the present invention, as described herein.

Optionally elevated rim 47 may be provided in a plurality of optional sizes, lengths, and/or diameters. Optionally and preferably, rim 47 may be customized and/or adjusted relative to the height, direction and contour of the gingiva and/or pivot 12, according to the prosthodontic requirements.

Optionally elevated rim 47 may be about 7 mm in length. Optionally elevated rim 47 may be at least from about 0.5 mm or more. Optionally elevated rim 47 may be provided with a standard size that may be adjusted and/or customized by a practitioner as needed according to the individual morphology and related prosthodontic requirements.

Optionally and preferably interface member 40 allows for mounting abutment pivot 12 inside anchor 32 before the perio-implant tissue heals, and further allows mounting to be carried out without injuring the gum again. Thus, abutment assembly 10 and members thereof may be mounted in one stage without interfering with the tissue healing process, resulting in a healthy biologic width.

Optionally elevated rim 47, FIGS. 8A-F, may be used as a platform for engaging the prosthodontic restoration 5, when mounted on abutment 10.

Optionally and preferably elevated rim 47, FIGS. 8A-F, may further provide for engaging at least one or more sleeve 50 and/or sleeve assembly 50s, 52, 54. Optionally and preferably elevated rim 47, FIGS. 8A-F, may further provide for engaging composite materials.

Optionally and preferably elevated rim 47 may be customized, adjusted, sized and/or contoured with respect to the gingival tissue and in relation to pivot 12 to provide abutment assembly 10 with the correct position, shape and geometry while conforming to the prosthodontic requirements. Optionally and preferably elevated rim 47 may be adjusted, sized and/or contoured with respect to the occlusal plane, gingival tissue in relation to pivot 12, most preferably to substantially assume an angle of about 90 degrees, such that elevated rim 47 is substantially orthogonal and/or perpendicular with pivot 12.

Optionally rim 47 may be adjusted, contoured and/or shaped with tools as is known in the art and/or with dedicated tools.

Most preferably adjusting rim 47 according to the gingival tissue and pivot 12 provides for defining flange 46a forming a finish line. In particular flange 46a may be contoured and positioned in concordance with: the gingival tissue, the distance from the alveolar bone to ensure the appropriate transmucosal collar (of abutment assembly 10), biologic width and marginal seal according to the prosthodontic requirements.

Optionally and preferably, the defined finish line about flange 46a provides a marginal fit and passive support for at least one or more of restoration 5 margins and/or surface, sleeve 50 and/or sleeve assembly 50s, 52, 54 associated therewith allowing for an appropriate fit with interface member 40.

Most preferably the finish line defined by flange 46a, is adjusted and contoured to have sufficient thickness so as to ensure that at least one or more of restoration 5, sleeve 50 or sleeve assembly 50s, 52, 54 associated therewith form an emerging profile therein ensuring that the external surface of interface member 40 emerges with the profile of restoration 5.

Most preferably the finish line defined by flange 46a, is adjusted and contoured to have sufficient thickness so as to ensure that at least one or more of restoration 5, sleeve 50 or sleeve assembly 50s, 52, 54 associated therewith are provide durable thickness.

Optionally interface member 40, may be configured with a plurality of optional diameters, between apical end 40a and occlusal end 40b, defining transgingival portion (collar) 49. Optionally interface member 40 may have a uniform diameter about the length of interface member 40, for example as shown in FIGS. 8A-B. Optionally, interface member 40 may be configured to have at least two or more or plurality of diameters along its length, for example as shown in FIGS. 8C-E.

Optionally collar 49 may have different profiles for example including but not limited to gradually increasing slope, gradually decreasing slope, stepwise profile, curvy, concave, convex profile or the like profile. Most preferably collar 49 is provided with a smaller diameter than that of anchor 32, preferably to provide for platform switching and/or shifting to improve biological seal so as to preserve the alveolar bone level. Optionally collar 49 may be at least 2 mm long defined between the alveolar ridge and finish line 46a.

Optionally interface member 40 may be provided with size (diameter, height) relative to the size (diameter) of anchor 32. For example, rim 47 may be narrower, wider, or equal in diameter relative to that of anchor 32. Optionally elevated rim 47 may be shaped according to any geometric shape for example including but not limited to cylindrical, conical, polygonal having n sides (wherein n is at least 3), or the like.

FIGS. 8A-B show optional views of interface member 40 having an elevated rim 47 comprising diameter equal to that of implant anchor 32 about both apical end 40a and occlusal end 40b.

FIGS. 8C-E show optional views of interface member 40 having an elevated rim 47 comprising a diameter larger than that of implant anchor 32. Optionally the diameter of elevated rim 47 may be phased-in between apical end 40a and occlusal end 40b, gradually having a slope for example as shown in FIG. 8E.

Optionally the diameter of elevated rim 47 may not be phased, therein forming a shoulder for example as shown in FIG. 8D.

Optionally the diameter of interface member 40 may be provided with at least two diameters along the elevated rim 47. Optionally the apical end 40a may be provided relative to the diameter of anchor 32 such that it is wider, narrower and/or equal in diameter to that of anchor 32 at the apical end 40a and may change in diameter along its length, to provide for platform switching.

Optionally and most preferably the height of interface member 40 and elevated rim 47 must be provided such that it is at least 1 mm, to provide for a biologic width. FIG. 8F shows an optional interface member 40 that has been adjusted about rim 47 to form a contoured interface member 40 having a flange 46a defining the finish line. Optionally by contouring rim 47, flange 46a may assume optional shapes for example including but not limited to oval, elliptical, Most preferably flange 46a is perpendicular with the axis of pivot 12, for example as shown in FIGS. 2A-B. Most preferably the adjustments made to interface member 40 about rim 47 were made according the gingival tissue and to the adjustment made to pivot 12 of FIGS. 2A-B. The adjustments made to interface member 40 allow a practitioner to fulfill the prosthodontic requirements by customizing abutment assembly 10 about interface member 40 and pivot 12, where the adjustments are based on and are relative to the patient's morphology and prosthodontic requirements.

Referring now to FIGS. 9-11 showing optional embodiments of optional sleeves 50, 50s, 52, 54 utilized with abutment assembly 10, for example as shown in FIG. 1, 2A-B. Sleeve 50, 50s may be utilized as an adapter between pivot 12 and prosthodontic restoration 5, most preferably provided to couple a prosthodontic restoration 5 of substantially any size and shape with pivot 12 of abutment assembly 10.

Optionally sleeves according to the present invention, may be realized as a single sleeve member 50 or as a sleeve assembly 50s comprising at least two or more sleeve members, for example inner sleeve 52 and outer sleeve 54. Most preferably sleeve assembly 50s members are configured to be concentric and/or telescopic with one another. Optionally and preferably second sleeve 54 may have a diameter slightly larger than the diameter of the first sleeve 52, and may be telescopically mounted about the first sleeve 52. Optionally sleeve assembly 50s members 52, 54 may be secured and/or passively coupled to one another by friction and/or by suction.

Optionally sleeves 50 and/or members of sleeve assembly 50s, 52, 54 may be provided with textured internal or external surfaces. Optionally sleeve internal surface and/or external surface may be provided with threading.

Optionally sleeve 54 may be provided to couple and/or be integrated with restoration 5 to form a customized bore 5a that in turn is customized to receive inner sleeve 52.

Optionally, sleeves 50, 50s, 52, 54 may be made of biocompatible materials for example including but not limited to plastics, carbon fiber, fiberglass, acrylics, polymers, antibacterial metals or alloys thereof, titanium, titanium alloy, tantalum, tantalum alloy, zirconium, gold the like or any combination thereof.

Most preferably sleeves 50, 50s, 52, 54 comprises an apical end 50a, and an occlusal end 50b and a passage there through defining lumen 50c. Most preferably, apical end 50a provides for interfacing with anchor 32 and/or interface member 40. Most preferably occlusal end 50b is positioned toward the occlusal plane. Most preferably the axis of sleeve lumen 50c is provided for interfacing with pivot 12 along its length about occlusal portion 12a. Most preferably sleeve lumen 50c provides for receiving and/or housing composite and/or filling material so as to couple sleeve 50, 50s, 52, 54 onto a structure most preferably pivot 12 about occlusal portion 12a.

Optionally and preferably sleeve 50 may be of any size and/or shape and/or diameter and/or length.

Optionally sleeve 50, 52, 54 may be shaped to be cylindrical or conic. Optionally a conical sleeve, for example FIGS. 11B-C may provide an easier path of insertion and retrievability for mounting restoration 5. Optionally sleeve 50, 52, 54 may be provided with a different conical profile along its length. For example, about its apical portion 50a sleeve 50 may be provided with a Morse angle for example from about 1.4 degrees to about 2 degrees. Optionally the profile of sleeve 50, 52, 54 may be gradually increasing along its length between apical end 50a and occlusal end 50b.

Optionally sleeve 50, 52, 54 may be provided with a plurality of optional geometry and/or shape such that it may be provided with opposite walls that are substantially parallel.

Optionally, sleeve 50 and/or sleeve assembly members 50s may comprise an anti-rotational surface and/or geometry and/or texturing about at least one surface. Optionally anti-rotation surface may for example include but is not limited to a flat surface, hourglass shape, FIG. 8, hyperboloid, ellipsoid, polygonal surface of n sides (where n is at least 3), any shape thereof or the like. Optionally the anti-rotation surface may be provided relative to inner bore 5a of prosthodontic restoration 5 and/or outer sleeve 54.

Optionally sleeve 50 and/or sleeve assembly members 50s may be provided with opposing walls that are substantially parallel and/or surfaces to substantially increase the retention and resistance form of restoration 5.

Optionally the inner surface of the sleeves 50, 52, 54 may include a texture surface providing a better engagement with the filling material disposed therein. Preferably sleeves 50, 52 may be provided with smooth, straight, surface having no irregularities or undercuts ensuring complete seating and durability of restoration 5. In addition sleeve 50, 52 may optionally be provided with an inner threading along lumen 50c for engaging pivot 12, for example as shown FIG. 9B.

As indicated above, optional sleeves, according to the present invention, provide for interfacing and/or coupling between abutment pivot 12 and restoration 5 about bore 5a. Optionally sleeves 50, 50s, 52, 54 may be coupled or otherwise associated with pivot 12 directly by way of threading with engageable portion 13 or indirectly by way of composite buildup and/or filling materials, provided within sleeve lumen 50c interfacing with pivot 12 about occlusal portion 12a.

Optionally filling material may be selected for optimally engaging portions 13, 14 defined on pivot 12, and flange 46, for example about protrusion 48. The filling material may be a biocompatible composite or acrylic material, with or without adhesive proprieties, such as known in the dental art.

Optionally sleeves according to the present invention may be provided to interface with interface member 40. Optionally, the diameter of the sleeve 50, 52 may be configured to be smaller than the peripheral diameter of flange 46, 46a of interface member 40. For example, when abutment pivot 12 is mounted inside implant anchor 32 through the interface member 40, the sleeve's apical end 50a bears against the internal surface of interface 44 of member 40 and/or the internal surface of rim portion 47, and/or on the inner portion of finish line formed by flange 46a, for example as shown in FIGS. 2A-B.

FIGS. 9A-C show optional views and embodiments of sleeve 50 and inner sleeve 52, that may optionally be substantially similar and/or interchangeable with one another. FIG. 9A shows an optional sleeve 50, 52 that may be placed over pivot 12. Optionally sleeve 52 may be associated or otherwise coupled with pivot 12 in a plurality of optional means for example including but not limited to composite, threading or the like. Sleeve 52 comprises an apical end 50a and an occlusal end 50b. Optionally lumen 50c may be provided as a hollow member. Optionally sleeve lumen 50c may be provided with an internal surface having at least one or more threaded portions 52t, or having and inner textured surface and/or having a smooth inner surface.

Optionally the outer surface of sleeve 50, 52 may be provided with a textured surface, smooth surface, threading, or the like.

FIG. 9B shows a cross section view of an optional embodiment of sleeve 50, 52 a having a threaded portion 52t within the sleeve lumen 50c about its inner surface, as shown. Most preferably threaded portion 52t may be provided for associating and coupling with engageable portion 13 disposed about pivot 12. Optionally threaded portion may span the full length of the inner sleeve lumen 50c. Optionally threading may be disposed along the length of inner surface of sleeve lumen 50c in any portion and/or manner for example continuous, intermittent, medial section, distal section, proximal section, any combination thereof.

Most preferably sleeve 50, 52 comprises an external surface that is a smooth, straight surface without irregularities or undercuts, while the inner surface and/or lumen 50c may comprise threading and or texturing.

FIG. 9C shows an optional sleeve 50, 52 comprising at least one or more recesses 52r about the apical end 50a of sleeve 52. Optionally and preferably recess 52r provides for making sleeve 50, 52 pliable over its apical end 50a so as to ensure proper fit about the apical end 50a with corresponding member of abutment assembly 10. Optionally the apical end 50a may be further provided with a slope and/or inclination 52s as shown. Optionally inclination 52s may be provided in the form of a Morse angle and/or slope to interface with interface member about flange 46, 46a, or internal surface 44, for example as shown in FIG. 2B. Optionally inclination 52s may be provided to interface with flange 46a, 46. Optionally the surface of inclination 52s may be provided as a smooth or textured surface, or the like.

Figures 10A, 10B:
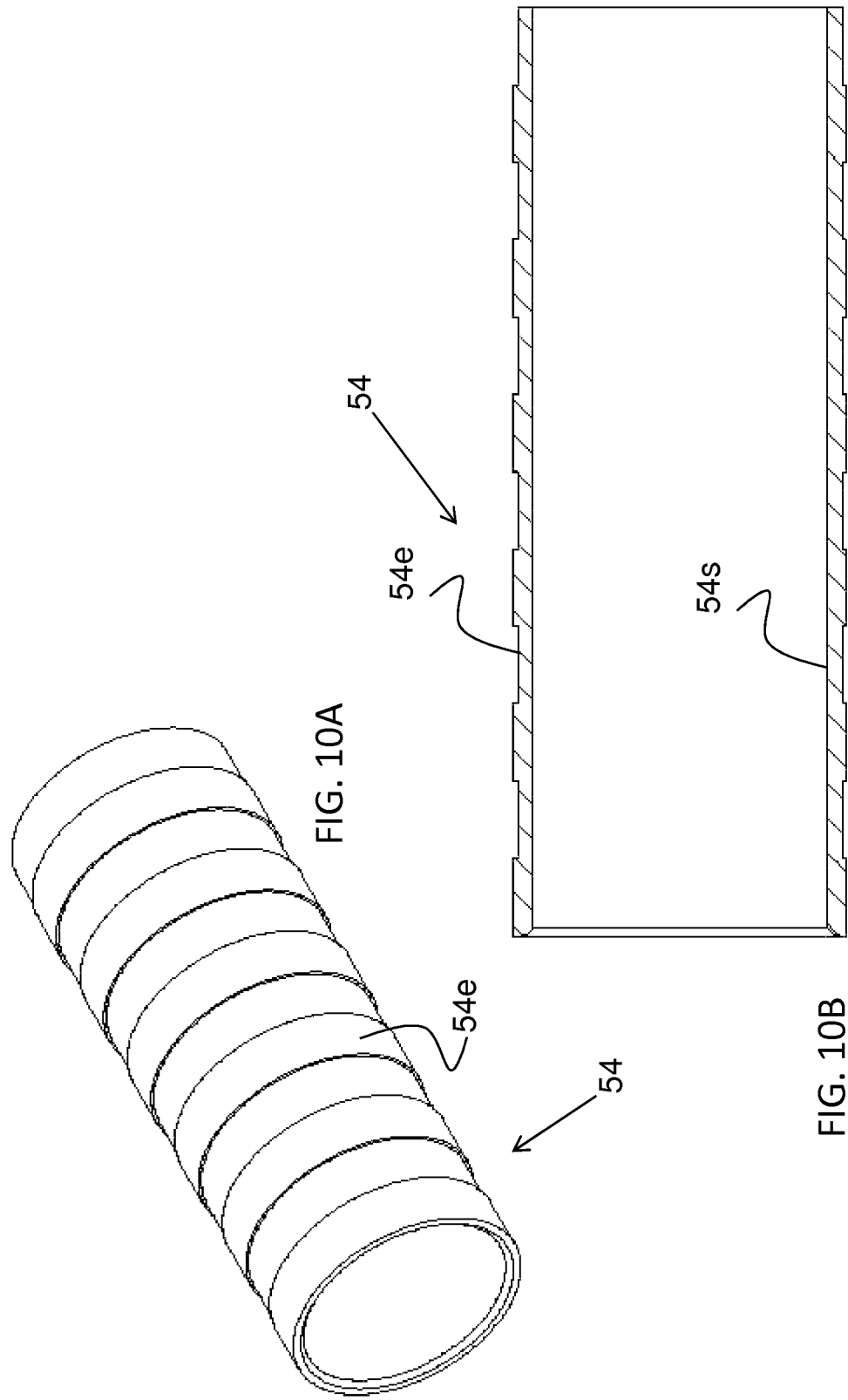
FIGS. 10A-B show various views of a schematic illustration of optional external sleeve members according to an optional embodiment of the present invention.

FIG. 10A shows an optional outer sleeve 54, while FIG. 10B shows a cross section view of outer sleeve 54 of FIG. 10A. Optionally and preferably the inner and/or luminal surface 54s of outer sleeve 54 may be provided such that it may interface and securely fit with inner sleeve 52, most preferably by passive means for example including but not limited to friction and/or by suction, providing for passive retention of restoration 5. For example, luminal surface 54s may be smooth, and most preferably provided to interface with the corresponding external surface of an inner sleeve 52e, for example as shown in FIGS. 9A-C.

Optionally outer sleeve 54 may be provided with an external surface 54e having a non smooth profile, threading and/or texture, for example as shown having a plurality of recessed rings along its length. Optionally external surface 54e provided with an increased surface area, as shown, improving coupling and/or interfacing with mounting bore 5a.

Optionally sleeve 50, and sleeve assembly 50s members 52, 54 may be provided with optional shapes about either of its internal or external surfaces and/or profiles for example including but not limited to cylindrical, conical, elliptical, hourglass, "figure 8", hyperboloid, ellipsoid, octagonal, hexagonal, polygonal with n sides (where n is at least 3), any combination thereof or the like. Optionally sleeves 50, 50r, 50s, 52, 54, 52b, 54b may be provided with a variable radius and/or a plurality of radii along its length, for example to assume a plurality of optional shapes. For example a sleeve may assume a bottle shape and/or profile in a sleeve having two radii about its length a first radius about its apical end 50a and a second radius about its occlusal end 50b, where a transition location about the length of the sleeve defines a sleeve shoulder forming a bottle neck. Optionally and preferably the sleeve surface may be configured such that it provides an anti-rotational surface.

Optionally the shape of bore 5a may be customized according to the shape of sleeve assembly 50s. For example, once sleeve assembly 50s is adjusted and sized about abutment pivot 12, outer sleeve 54 may be removed and utilized to shape and customize bore 5a of restoration 5, therein sleeve 54 may form a customized bore 5a. Most preferably this ensures proper fit and marginal seal of abutment assembly 10 with restoration 5. This way, the technician preparing the prosthodontic restoration 5 may be provided with the second sleeve 54 for mounting inside the mounting bore 5a, and thus the bore 5a may be formed with the corresponding shape of abutment assembly 10. When the practitioner then mounts prosthodontic restoration 5 comprising bore 5a formed from sleeve 54, on abutment assembly 10, the prosthodontic restoration 5 may be retainably mounted on the abutment merely by sliding the second sleeve 54, disposed inside the mounting bore 5a, on the first sleeve 52 mounted on abutment assembly 10 about pivot 12.

Most preferably this configuration achieves high level of friction between members of sleeve assembly 50s due to the corresponding fit between the surfaces of the inner sleeve 52 and the outer sleeve 54, providing passive retention of the prosthodontic restorations. Thus, the prosthodontic restoration 5a may be easily placed on the abutments and passively retained thereon. Optionally and preferably, this concentric and/or telescopic configuration about sleeve assembly 50s members further provides for the retrievability of restoration 5 from pivot 12, as may become necessary. Most preferably retrievability of restoration 5 provides for the ease of removing the prosthodontic restoration 5 without causing any damage to a restoration 5 itself and/or the abutment assembly 10. This is particularly useful when the prosthodontic restoration 5 has to be removed to allow for additional maintenance of restoration 5, abutment assembly 10, anchor 32, or the host tissue.

FIGS. 11A-B show an optional embodiment for a rimmed inner sleeve 52b and outer sleeve 54b corresponding thereto. Most preferably inner sleeve 52b comprises a rim portion 53 provided to increase the diameter of sleeve 52b providing a base that is most preferably wider than the diameter of interface member 40. Optionally and preferably rim 53 provides and defines a finish line for abutment assembly 10. Most preferably rim 53 provides a finish line platform onto which restoration 5 may be placed in accordance with the biomechanical principles. Most preferably rim portion 53 is provided such that it may rest about flange 46, 46a or interface member 40 and effectively provides for widening flange 46, 46a, or the occlusal end of anchor 32. Most preferably rimmed inner sleeve 52b is further provided with a coupling portion 52c provided for associating with interface member 40 about aperture 43 and/or internal surface portion 44. Optionally coupling portion 52c may be configured directly couple and/or associate with an anchor 32 about a bore 36. Optionally coupling portion 52c may be configured to couple and/or associate with an external interface disposed about anchor 32 for example in the form including but not limited to an external hex. Optionally the shape of sleeve 52b may be cylindrical and more preferably conical, as shown.

Most preferably rim portion 53 provides for further associating with outer sleeve 54b, that in turn associates with restoration 5 optionally and most preferably about bore 5a.

Optionally and preferably inner sleeve 52b and outer sleeve 54b comprise corresponding male/female coupling members provided as anti-rotational measures for preventing outer sleeve 54b from rotating about inner sleeve 52b. For example pegs 54L disposed about outer sleeve 54b may be provided to associate with a corresponding anti-rotational recess 52d disposed about inner sleeve 52b, therein providing an anti-rotational measure.

Now referring to FIG. 11C shows a further optional embodiment for a sleeve 50r comprising a rimmed portion 53. Optionally sleeve 50r may be provided as a standalone sleeve 50, or as a member of sleeve assembly 50s for example in the form of an inner sleeve 52 or outer sleeve 54. Most preferably sleeve 50r comprises an apical end 50a, an occlusal end 50b and a lumen 50c, as previously described. Optionally apical end 50a of sleeve 50r may be provided with a contoured surface provided for associating and/or interfacing with aperture 43 and/or portion 44 of interface member 40. Most preferably rim portion 53 may be adjusted to securely fit with and/or over flange 46a. 46. Optionally and preferably rim portion 53 may be contoured and shaped in relation to the contour and shape of flange 46, 46a. Most preferably rim portion 53 may be provided to close and/or cover aperture 43 of interface member 40 over flange 46, 46a. Most preferably rim portion 53 may form the finish line. Optionally and preferably when sleeve 50r comprising rim 53 is realized in the form of an outer sleeve 54 it provides a marginal fit with the restoration 5.

An optional embodiment of the present invention, similar to that described and shown in FIGS. 11A-C, provides for creating a finish line for abutment assembly 10 with a dedicated finish line member (not shown) functioning similarly to rim 53 described above. The finish line member may for example be provided in the form of a washer or the like disk like and/or ring like structure that may interface with flange 46, 46a, sleeve apical end 50a, or directly with the occlusal end of anchor 32. Optionally, sleeve 50, 50s, 52, 54 may come into contact with a washer, or the like ring structure (not shown), disposed over interface member 40 about flange 46, 46a. Optionally the finish line member for example in the form of a washer (not shown) may have a peripheral diameter larger than the diameter of interface member 40 and an inner diameter smaller than sleeve 50 and interface member 40, therein configured to allow sleeve 50 to rest about the surface of the washer while the washer rest on the flange 46, 46a of interface member 40. The washer may be disposed on flange 46, 46a of elevated rim portion 47 and about pivot 12. Thus, when the sleeve 50 is affixed to the pivot 12, the apical end 50a bears against the washer onto which restoration 5 is placed. Optionally a second sleeve member 54 may also be coupled over abutment assembly 10 comprising the washer. It is appreciated that the finish line member for example in the form of a washer may be selected in accordance with the diameter of the sleeve 50, interface member 40, and pivot 12. This way, the interface member 40 may be used with a sleeve having any desired diameter, regardless of the diameter of the interface member 40. An optional embodiment provides a sleeve comprising a stopping member (not shown) disposed about the inner and/or luminal surface 50c of sleeve 50, 52. Optionally and preferably stopping member may be provided to act as a shock absorber and/or as a plastic force absorption point. Optionally stopping member may for example be provided in the form of an integrated nut disposed about the lumen of sleeve 50, 52. Optionally and preferably stopping member provides for associating with pivot 12 about occlusal portion 12a. Most preferably the stopping member prevents and/or delays breakage of pivot 12 when undue forces are applied when adjusting pivot 12. Most preferably stopping members provides a predefined and configured shock absorber and/or structural breaking point and/or absorption point and/or force absorption point and/or plastic point, configured such that stopping member and sleeve 50, 52 absorb any undue forces applied onto pivot 12 while it is adjusted, therein preferably maintaining the structural integrity of pivot 12.

An optional embodiment provides for sleeveless mounting of restoration 5 about abutment assembly 10 and particularly pivot 12. Optionally, sleeve 50, 52 may serve as a mold for forming composite buildup about occlusal portion 12a of pivot 12. The mold may be formed by inserting a moldable filling material inside a sleeve mounted on pivot 12, and optionally removed after is formed around occlusal portion 12a. Optionally such composite buildup may provide for directly mounting and/or coupling prosthodontic restoration 5 onto pivot 12 interfaced with the composite build up disposed thereon.

Now referring to FIGS. 12A-D showing perspective views of an optional long closing nut 70 FIGS. 12 A-B and FIGS. 12C-D showing a similar view of an optional short closing nut 70. FIGS. 12B and 12D show respective sectional views of closing nut 70 of FIGS. 12A and 12C.

Most preferably nut 70 may be provided with an abutment end 70a provided for coupling to abutment assembly 10 about pivot 12 and a restoration end 70r interfacing with restoration 5. Preferably the internal threading about abutment end 70a provides for coupling to abutment 10 about pivot 12 with the corresponding threading about engageable portion 13. Preferably the internal threading about restoration end 70r may provide for coupling a restoration closing surface element, for example locking nut plug 72 (not shown) having corresponding threading.

Optionally and preferably nut 70 may be provide with a stepped external surface 70c, as shown, disposed about its abutment end 70a, for centering and locking nut 70 with abutment assembly 10 and/or sleeve 50, 52.

Optionally and preferably, locking nut plug 72 (not shown) may be provided cover and close the surface of restoration 5. Most preferably locking nut plug 72 provides for closing and interfacing between restoration end 70r of locking nut 70 and restoration 5. Optionally plug 72 may be provided with optional surfaces to complete the occlusal surface of restoration 5. Optionally plug 72 may be provided from the same materials of restoration 5.

Figure 13:
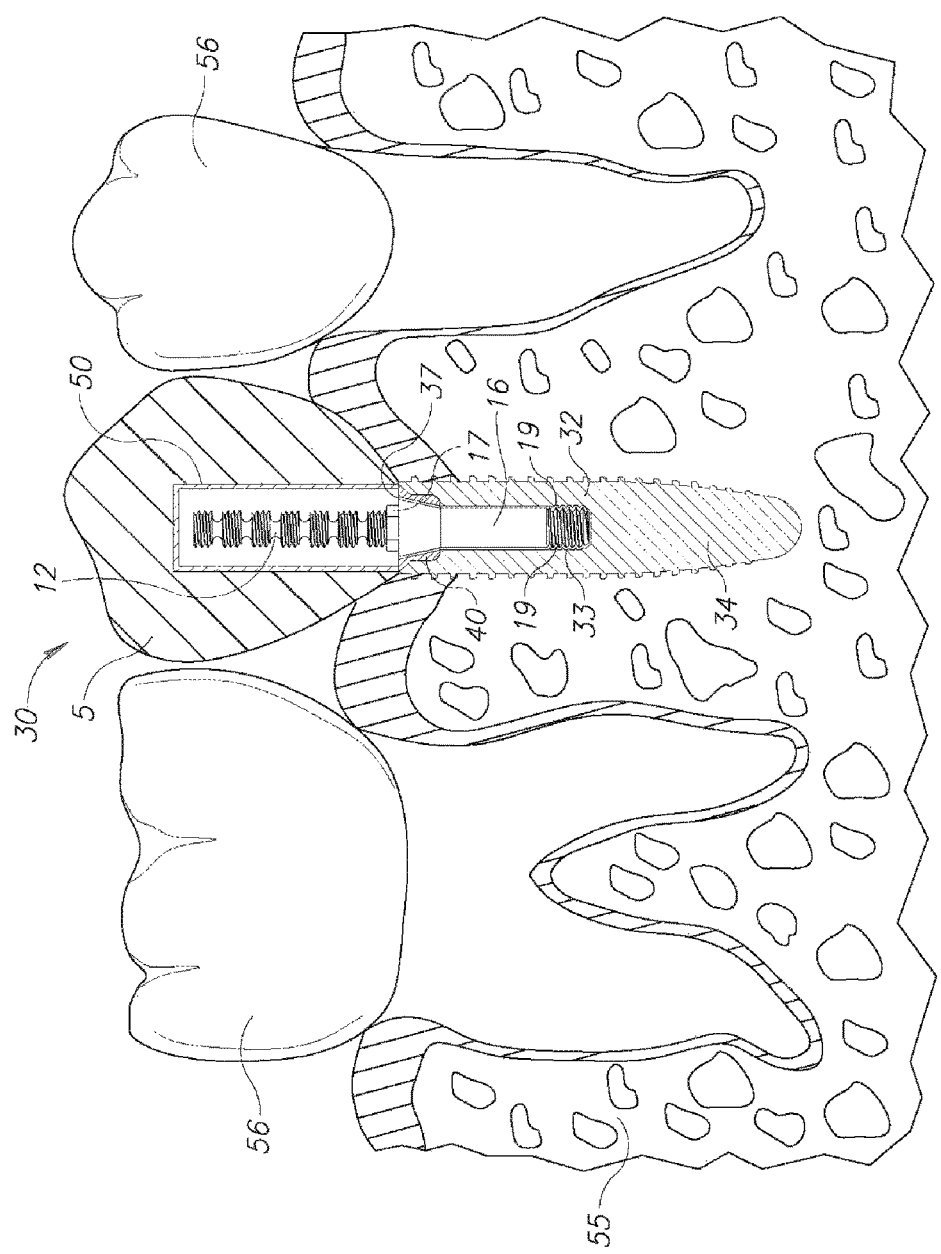
FIG. 13 is side sectional view of a dental implant system, shown in FIG. 1, comprising the abutment pivot of FIGS. 2A-C, after implantation, according to an optional embodiment of the present invention.

FIG. 13 is a side sectional view of a jawbone 55, having dental implant 30 as illustrated in FIG. 1 implanted therein, between natural teeth 56, in accordance with one example of the presently disclosed subject matter. Dental implant 30 is secured to jawbone 55 by screwing therein screw thread 34 defined on the outside periphery of anchor 32, functioning as a natural root of a tooth. Interface member 40 is disposed in opening 37 of bore 36 in a manner which allows hexagonal portion 42 to interface hexagonal interface 38 defined about the inner periphery of opening 37, thus precluding the rotational displacement of interface member 40.

Pivot mounting member 16 disposed about the apical end of abutment pivot 12 is inserted in bore 36 of anchor 32 after insertion thereof, through aperture 43 of interface member 40. Pivot mounting member 16 may be fastened to anchor 32 by means of threading 19 at the apical end of abutment pivot 12 and a corresponding screw thread 33 defined at least about a portion of the inner periphery of bore 36. Rotation of abutment pivot 12 for fastening screw thread 19 and corresponding screw thread 33 may be carried out by means of engaging a tool, such as a wrench, with a screw head interface 17, or optionally by means of dedicated tools therefore.

When mounting member 16 of abutment pivot 12 is fully inserted in bore 36, stabilizing portion 15 preferably engages corresponding cone portion 44 defined about the inner surface of aperture 43. The downwardly slope of stabilizing portion 15 more evenly distributes the forces applied by the prosthodontic restoration through the sleeve 50, the pivot 12, and the anchor 32, onto the bone 55 underneath. It will be appreciated that interface member 40 may be disposed in such a way that flange 46 is level with the margin of the anchor 32 or alternatively is elevated from the anchor, for example with elevated rim 47, in accordance with the morphologic and restorative requirement. Most preferably the arrangement about abutment assembly 10 and further transfers the forces through the pivot 12, the stabilizing portion 15, the mounting member 16 and anchor 32 to the bone. In addition, the core arrangement allows for peripherally transferring the forces through the filling material and at least one of sleeve 50 and/or outer sleeve 54 of sleeve assembly 50s, to the interface member 40 about flange 46 and the anchor, onto the bone.

In addition, forming the abutment assembly 10 with the required position, geometry and shape provides the restoration with the optimal path of insertion and retrievability, leading to passive support and passive retention. That is to say, that the abutment assembly 10 of the presently disclosed subject matter allows for mounting the restoration 5 passively thereon with optimal contact therebetween, preferably without the use of adhesive material and optionally with a retaining screw 70 and plug 72 (not shown).

Figure 14A:
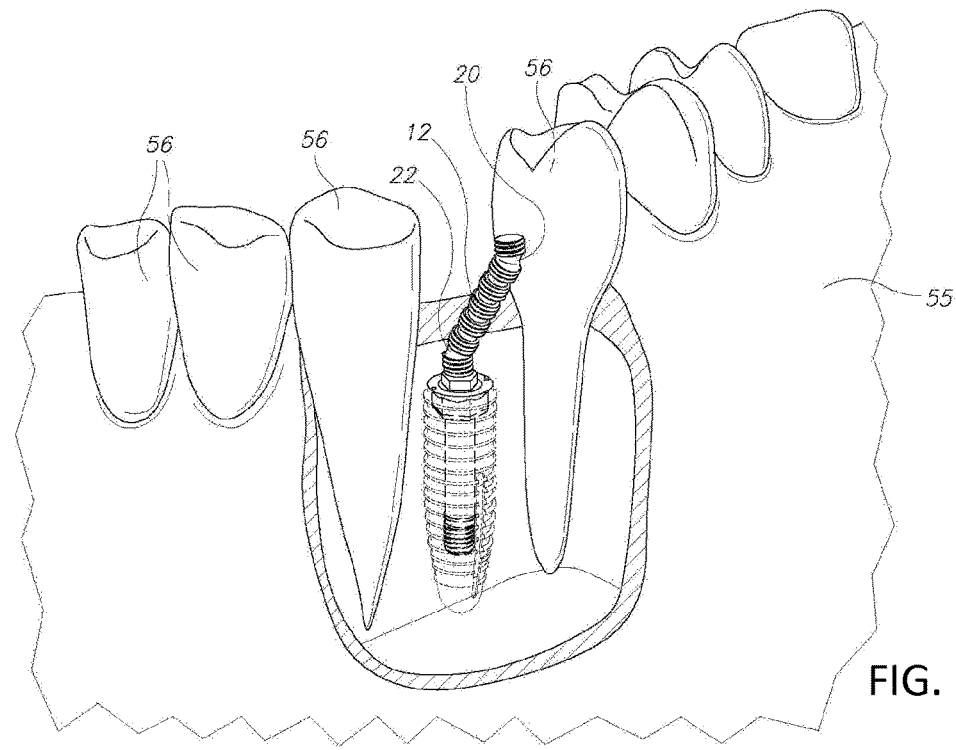
FIGS. 14A-B are partial cut away perspective views of optional stages during implantation of a dental implant system of FIG. 1, showing an adjusted abutment pivot, FIG. 14A, and a mounted sleeve, FIG. 14B, according to an optional embodiment of the present invention.
Figure 14B:
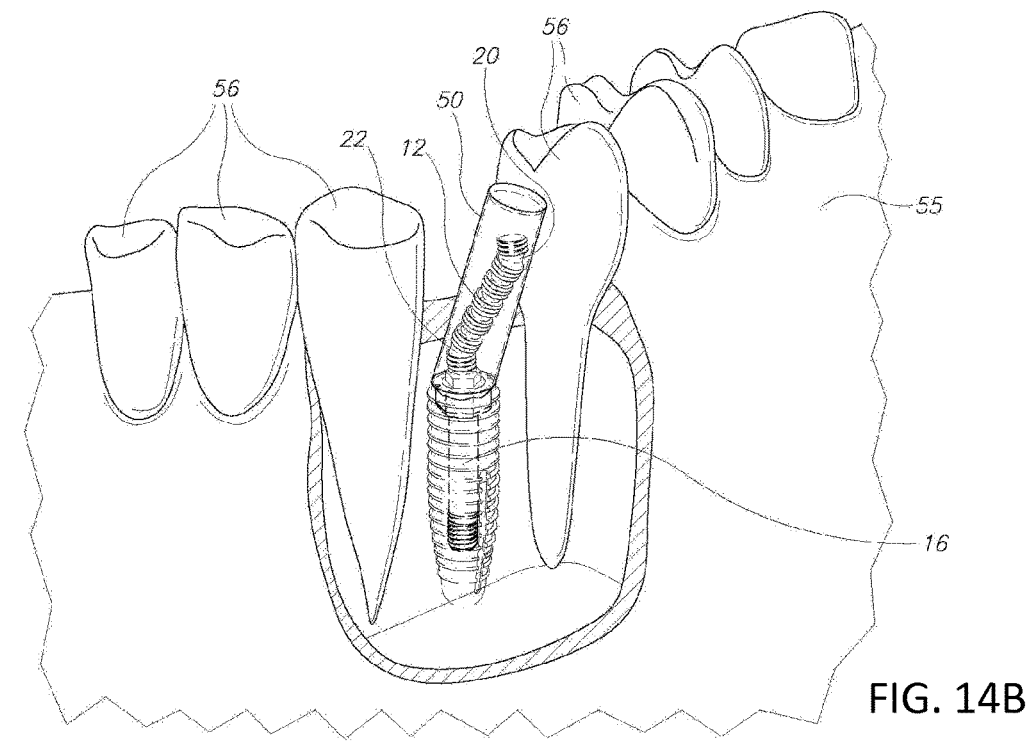

As best seen in FIGS. 14A and 14B, pivot 12 may be adjusted at a desired position so as to allow appropriate alignment of the abutment assembly 10 with respect to other abutments and/or residual teeth on the same and opposite jaw. Pivot 12 may be adjusted in more than one location along its length, about at least one or more adjustment portion 14, so as to achieve the appropriate positioning of pivot 12. For example, pivot 12 may be adjusted to assume a first angle 20 at its apical portion and may be adjusted further to form a second angle 22 on an occlusal portion thereof, so as to achieve the required position and shape of the abutment assembly 10. Most preferably, adjusting pivot 12 may be carried out when abutment 10 is securely fixed and/or coupled with anchor 32. Optionally abutment pivot 12 may be configured and/or adjusted by a clinician outside of the patient's mouth, after the appropriate prosthodontic requirements and measurements have been considered in order to determine the position and shape of abutment 10 prior to securely coupling with anchor 32.

Once the direction, angle and length require for pivot 12 are determined, sleeve 50 or sleeve assembly 50s may be disposed over pivot 12, with or without filling material therebetween. Optionally once sleeve 50 or inner sleeve 52 is fully disposed over pivot 12, the apical end of sleeve 50a abuts flange 46, 46a of interface member 40. The filling material inside sleeve 50 or inner sleeve 52 optionally engages optional protrusion 48, and/or portions 13/14. Once filling material inside of sleeve 50 or inner sleeve 52 of sleeve assembly 50s is cured, it precludes rotation or removal and/or sliding of the sleeve 50 or inner sleeve 52 about pivot 12.

Optionally when utilizing sleeve assembly 50s inner sleeve 52 and outer sleeve 54 are both adjusted to securely fit over pivot 12 in a concentric manner where, inner sleeve 52 is associated or otherwise coupled with pivot 12, as described above with respect to sleeve 50, then sleeve 54 may be adjusted with respect to sleeve 52 and disassociated therefrom. Outer sleeve 54 may then be associated with restoration 5 about bore 5a, as previously described, to defining a path of insertion for restoration 5 that is specific to the configuration of inner sleeve 52 and therein pivot 12.

Most preferably, this arrangement provides for optimal marginal fit between abutment assembly 10 and restoration 5 as the marginal fit is mediated via the members of sleeve assembly members 50s, for example outer sleeve 54 (now part of restoration 5) and inner sleeve 52 (now part of abutment assembly 10 over pivot 12).

Thereafter, prosthodontic restoration 5 may be mounted on sleeve 50, or alternatively it may be mounted directly over pivot 12, with or without a filling material.

Optionally a sleeveless configuration may be similarly fit wherein composite material is associated with pivot 12 over engageable portion 13, following customization and adjustment of abutment assembly 10 and in particular pivot 12 and/or interface member 40. Composite material over pivot 12 may be customized to mediate between restoration 5 about bore 5a and abutment assembly 10 about pivot 12.

Figure 15:
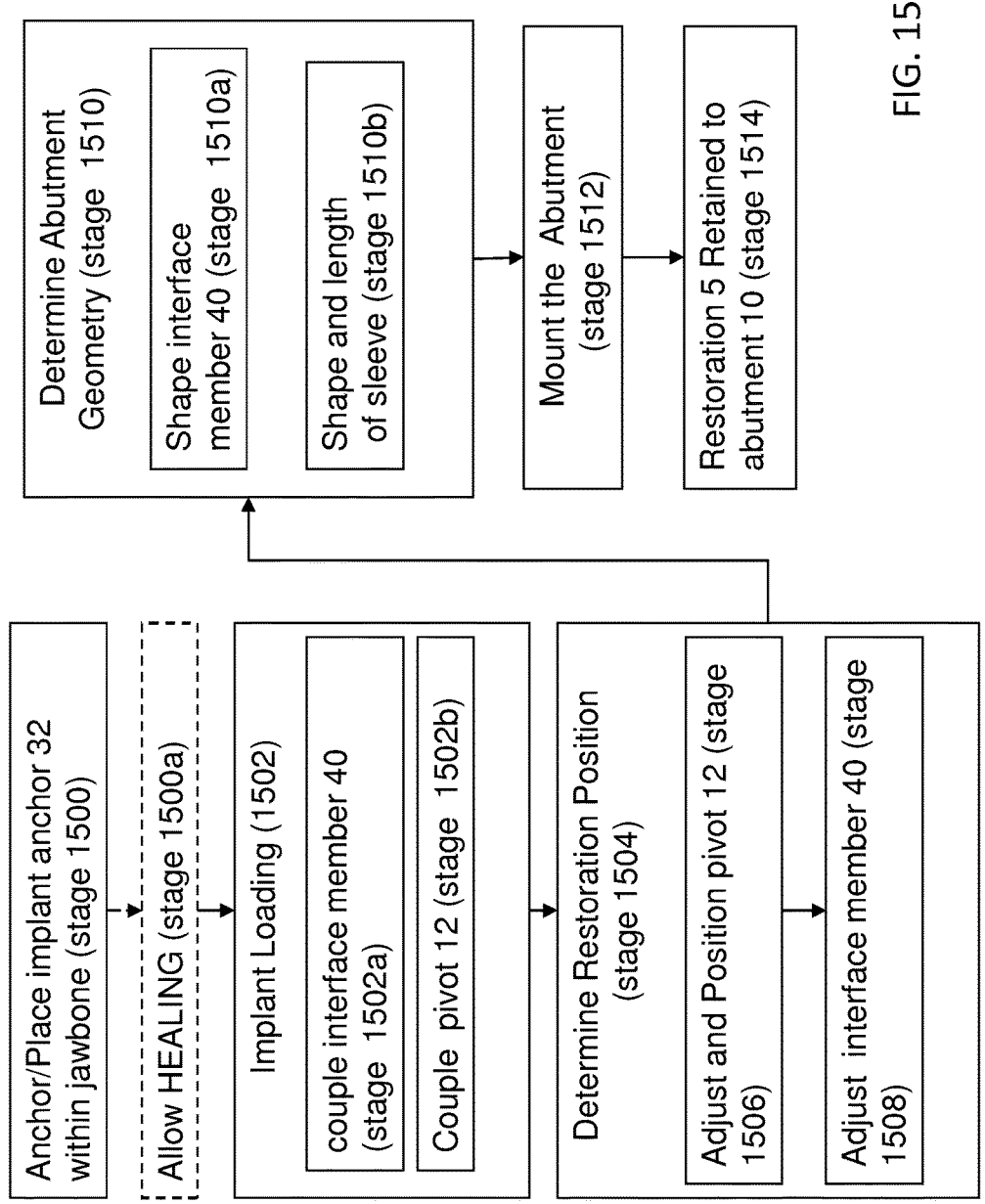
FIG. 15 shows a flowchart of a method according to an optional embodiment of the present invention.

Now referring to FIG. 15 showing a flowchart depicting an optional methods for placing a dental implant system 30 comprising an abutment assembly 10 according to optional embodiments of the present invention. Most preferably utilizing abutment assembly 10 provides for adhering to the biomechanical principals and therein achieving implant's functional, biological and esthetic requirements.

First in stage 1500, the implant anchor 32 is placed within the jawbone according to methods as known in the art. Optionally placement of the implant anchor may be followed with an optional and appropriate healing time, as depicted in stage 1500a. Next in stage 1502 implant anchor 32 is loaded with an optional abutment assembly 10 according to the present invention. Implanting loading comprises an initial sub-stage 1502a for coupling and/or otherwise associating an interface member 40, optionally and preferably comprising an elevated rim 47, with the implant anchor 32 most preferably about bore 36. Next in a secondary sub-stage 1502b abutment pivot 12 is coupled or otherwise associated with anchor 32, with pivot mounting member 16, for example utilizing optional threading 19, 68 or the like threading and/or coupling means. Most preferably abutment pivot 12 is placed through interface member 40 aperture 43 to allow for coupling while stabilizing portion 15 interfaces with internal surface 44 of interface member 40.

Next in stage 1504 the position of abutment assembly 10 is determined, particularly by evaluating the individual's morphology and related prosthodontic requirements to determine the end position of restoration 5 that is to be mounted on abutment assembly 10.

Next in stage 1506, a practitioner adjusts abutment assembly 10 about abutment pivot 12 most preferably about occlusal portion 12a, for example about adjustment portion 14 as previously described. Most preferably adjustment of abutment pivot 12 is provided in accordance with the position determined in stage 1504 therein accounting for and customizing and/or adjusting in accordance with the individual morphology and related prosthodontic requirements of the patient. Preferably, pivot 12 is positioned to protrude substantially perpendicularly to the occlusal plane, and align substantially parallel with abutments and/or teeth of the same jaw. Preferably pivot 12 may be positioned during the procedure by clinician and/or practitioner by adjusting its angle and direction in relation to at least one or more of pivot mounting member 16, the axis of anchor 32, other abutments and/or residual teeth. Preferably, the vertical dimension of abutment 10 assembly may be determined by occlusal reduction, for example by filing or cutting, or by extending of pivot 12 as necessary, for example with pivot extender 12e, as previously described, to provide the necessary space about the occlusal plane for the structural durability of restoration 5. Optionally and preferably abutment 10 and in particular pivot 12 may be adjusted about occlusal portion 12a with off the shelf tools and/or dedicated and/or proprietary tools and/or pivot or abutment manipulators.

Once abutment pivot 12 is defined in accordance with individual morphology and related prosthodontic requirements to enable optimal positioning and fit of restoration 5, then interface member 40 is adjusted accordingly in stage 1508. Optionally stage 1506 and 1508 may be performed simultaneously and/or incrementally and/or interchangeably so as to ensure corresponding and/or correlated adjustment to pivot 12 and interface member 40. In stage 1508 interface member 40 is adjusted to adapt between implant anchor 32, the perio-implant tissues and abutment assembly 10 Interface member 40 may be individually adjusted, optionally and preferably the adjustment is provided on line and/or in real time, during and/or while the procedure is carried out by the clinician and/or practitioner. Optionally and most preferably interface member 40 is adjusted about rim 47 of interface member 40 such that it is apically reduced by cutting and/or filing in relation to the gingiva, and is adjusted to most preferably be substantially perpendicular (at about a right angle and/or orthogonal) with respect to pivot 12. Therefore most preferably adjusting rim 47 defines and forms the contour of flange 46a therein forming and defining a smooth finish line. Optionally and preferably smoothing the finish line may be provided with standard tool and or dedicated tools. Most preferably a smooth finish line provides for properly engaging and closely fitting the apical end 50a of optional sleeves 50 or sleeve assembly 50s members including sleeves 52, 54, 52b, 54b and/or the apical surface and margins of restoration 5. Optionally the finish line may be defined by rim 53 as previously described.

Most preferably the finish line defined by flange 46, 46a or rim 53 will most preferably be substantially parallel to the occlusal plane, and substantially perpendicular to pivot 12. Preferably the finish line will be located in an area that may be inspected easily by a clinician, cleaned while providing sufficient distance from the alveolar crest to allow the combined epithelial and connective tissue attachment to generate a healthy "biologic width". The perpendicular positioning of abutment assembly 10 in relation to the occlusal plane, and the perpendicular positioning of sleeve 54 and/or restoration 5 in relation to the finish line about flange 46, 46a, rim 53, preferably enables for passive support and passive retention increasing resistance form. In addition to being perpendicular to occlusal plane and finish line, the parallel positioning of abutment assembly 10 determines one path of insertion and retrieval for restoration 5, providing passive support and retention for restoration 5.

Next in stage 1510 the geometry of abutment assembly 10 is determined by adjusting interface member 40 and sleeve 50 or members of sleeve assembly 50s. In sub-stage 1510a interface member 40 is adjusted further to finalize its geometry, shape and length. Most preferably the diameter of the transgingival portion (collar) 49 of interface member 40, FIGS. 8A-B, may be adjusted. Optionally and preferably the diameter of transgingival portion (collar) 49 of interface 40 may be adjusted so as to be smaller than the diameter of implant anchor 32. Most preferably adjusting interface member 40 about collar 49 defines a free space along the anchor's contour providing for platform switching and/or platform shifting. Most preferably such fee spaces about collar 49 allows a space onto which hard tissue may proliferate overlapping the implant's contour and improving its fixation and biologic seal and/or preserving alveolar bone level. Optionally the reduced diameter of transgingival portion of interface member 40 at collar 49 restricts the contact surface between implant and perio-implant tissue, therein significantly improving the marginal seal of the implant. Most preferably the length of the transgingival portion defined between the alveolar ridge and finish line is optionally and preferably adjusted to be at least 2 mm in length ensuring the integrity of the biologic width.

Next in stage 1510b following adjustment of the transgingival portion of interface member 40 as described in stage 1510a, sleeve 50 or sleeve assembly 50s members are similarly adjusted about at least one of the sleeve's end, occlusal end 50b and/or apical end 50a. Optionally both ends of sleeve 50 and/or sleeve assembly 50s members may be adjusted as necessary. More preferably, adjustments are made about the occlusal end 50b and optionally to the apical end 50a. Most preferably, the adjustments about sleeve 50 and/or assembly 50s may be provided so as to form an occlusal surface 50b that is substantially parallel with the finish line surface for example defined by flange 46, 46a or rim 53. The length of sleeve 50 may be determined by the distance between the finish line and the occlusal plane. Most preferably the length of sleeve 50 is optimized to provide a larger surface area to ensure better retention between abutment assembly 10 members and restoration 5 via the intervening sleeve 50, 52. Preferably the length of sleeve 50 may be adjusted about its occlusal extremity 50b to become substantially parallel with the finish line defined by flange 46, 46a, rim 53. Therein the surface of occlusal end 50b and flange 46a, are most preferably adjusted to form substantially parallel surfaces, providing the necessary space about the occlusal plane to ensure the structural durability of restoration 5. Optionally the apical extremity 50a of sleeve 50 may also be adjusted to closely fit the finish line.

Next in stage 1512 abutment assembly 10 may be mounted so as to prepare it to receive restoration 5. Most preferably abutment assembly 10 is mounted about pivot 12 that may be accomplished by optional means for example including but not limited to composite build up about pivot 12 or by coupling at least one or more sleeve 50,52 about pivot 12.

Optionally, composite buildup about pivot 12 over occlusal portion 12a may be provided, as previously described, wherein filling materials, and/or composite materials may be shaped over pivot 12, for example about engageable portion 13. Optionally buildup about pivot 12 provides for shaping and forming composite materials that may later be directly coupled with restoration 5 about bore 5a.

Optionally pivot 12 may be mounted with sleeve 50, 52, 52b or members of sleeve assembly 50s. Optionally the method of coupling sleeve 50 or sleeve assembly 50s about pivot 12 depends on the type of sleeve utilized, for example as shown in FIGS. 9-11. Optionally sleeve 50 or inner sleeve 52, 52b comprising inner threading 52t about the luminal surface, for example as shown in FIG. 9B, may be threaded over pivot 12 to couple with engageable portion 13. Optionally sleeve 50 or inner sleeve 52, 52b may be mounted and/or coupled over pivot 12 with filling materials, composite materials or the like. Most preferably sleeve 50 or inner sleeve 52, 52b may be disposed over pivot 12 where the filling material is provided such that the inner lumen 50c is filled with filling materials and/or composite materials to allow the coupling of sleeve 50, 52 with pivot 12. Preferably coupling sleeve 50, 52 provides for firmly engaging the inner surface 43 of interface member 40 and/or the inner contour of the finish line defined about flange 46, 46a. Most preferably, after coupling sleeve 50 onto pivot 12 the outer contour of the finish line defined by flange 46a, 46, rim 53 is left with substantial width to receive restoration 5 and/or additional sleeves, such that the finish line properly fits with restoration 5 both horizontally and vertically defining a proper emerging profile.

Next stage 1514 restoration 5 is retained to abutment assembly 10. Most preferably restoration 5 may be coupled to abutment assembly 10 by optional means for example including but not limited to telescopic association, cementing, or rigid retainment or the like.

Optionally telescopic retainment may be provided when utilizing sleeve assembly 50s comprising inner sleeve 52, 52b and outer sleeve 54, 54b, where inner sleeve 52 is already coupled and/or associated with pivot 12, as described in stage 1512, now sleeve 54 is adjusted accordingly. First, the occlusal end 50b of outer sleeve 54 is adjusted such that it is slightly longer then sleeve 52. After length adjusted sleeve 54 is mounted over sleeve 52 so that sleeve 54 engages the finish line defined by flange 46a, 46, rim 53. Next restoration 5 is mounted over sleeve 54 and its profile adjusted about adjacent and opposite teeth and/or restorations until it's apical margins passively engages the finish line. Restoration 5 is then passively cemented onto sleeve 54. Optionally and preferably once the adjustment to sleeve 54 is finalized sleeve 54 may be cast and/or integrated with restoration 5 about bore 5a and thereafter mounted onto sleeve 52, 52b. Most preferably, retention of restoration 5 about sleeve assembly 50s is achieved by the passive contact and friction fitting between the surfaces of sleeves 52 and 54, where sleeve 54 slides over sleeve 52 along the path of insertion and retrieval.

Optionally mounting restoration 5 by way of cementing is most preferably provided by cementing restoration 5 with sleeve 50, 52 that are coupled and/or otherwise associated over pivot 12 as described in stage 1512.

Optionally and preferably sleeve 50, 52 may acts as a mold for composite materials and may be removed once composite material hardens and/or cures, therein leaving the molded composite material built up over pivot 12. Next, restoration 5 is mounted over the composite built up and it's profile is adjusted about adjacent and opposite teeth and/or restorations until the build up's apical margins passively engages the finish line defined about flange 46, 46a. Finally, restoration 5 is most preferably passively bonded and/or cemented to build up of abutment assembly 10.

A further optional method for retaining restoration 5 over abutment assembly 10 by way of cementing, may be provided by maintaining sleeve 50 intact, not removing it as described above, and directly cementing restoration 5 onto sleeve 50 over bore 5a. Optionally cementing restoration 5 via bore 5a, may be provided with a plurality of sleeves 50 bonded and/or fixed and/or otherwise coupled onto one another so as to provide a proper marginal fit between sleeve 50 and bore 5a of restoration 5.

A further optional method for retaining restoration 5 over abutment assembly 10 may be provided by way of rigid retainment. Preferably the occlusal extremities of abutment assembly 10 including sleeve 52 are adjusted such that sleeve 52 is reduced to lie slightly under the last occlusal threaded engageable portion 13 of pivot 12. Next locking nut 70 is threaded to engage engageable portion 13 of pivot 12. Optionally and preferably locking nut 70 may be threaded with pivot 12 through an aperture provided on the occlusal table of restoration 5. Most preferably locking nut 70 securely locks one or more of sleeve assembly member 50s, 52, 52b, 54, 54b, 50r and/or restoration 5 over pivot 12, most preferably over apical end 70a. Optionally and preferably locking nut 70 also provides for centering sleeve 52, sleeve assembly 50s with respect to the axis of pivot 12 via its external surface 70c comprising an appropriate profile, for example a stepped profile as shown, so as to fit the diameter of the sleeve being centered. Restoration 5 may then be mounted over sleeve 52. Optionally the profile of restoration 5 may be adjusted relative to adjacent and opposite teeth and/or restorations until it's apical margins passively engages the finish line for example defined by flange 46, 46a, or rim 53. Restoration 5 may then be passively cemented onto sleeve 52, and the aperture of restoration 5 may then be sealed optionally with a proper plug 72 and/or a filing as is known in dental art to complete the occlusal table of restoration 5.

Those skilled in the art to which the presently disclosed subject matter pertains will readily appreciate that numerous changes, variations, and modifications may be made without departing from the scope of the invention, mutatis mutandis.

There are many inventions described and illustrated herein. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

While the invention has been described with respect to a limited number of embodiment, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not described to limit the invention to the exact construction and operation shown and described and accordingly, all suitable modifications and equivalents may be resorted to, falling within the scope of the invention.

Having described a specific preferred embodiment of the invention with reference to the accompanying drawings, it will be appreciated that the present invention is not limited to that precise embodiment and that various changes and modifications can be effected therein by one of ordinary skill in the art without departing from the scope or spirit of the invention defined by the appended claims.

Further modifications of the invention will also occur to persons skilled in the art and all such are deemed to fall within the spirit and scope of the invention as defined by the appended claims.

While the invention has been described with respect to a limited number of embodiments, it will be appreciated that many variations, modifications and other applications of the invention may be made.

What is claimed is:

1. A dental implant abutment assembly for forming an individually customized dental implant abutment mounted on a dental implant anchor adapted to be implanted and having an internal connection platform, wherein the abutment assembly is individually customizable, the abutment assembly including:

a. an adjustable abutment pivot provided for coupling to the dental implant anchor, wherein said customized dental implant abutment is centered around said adjustable abutment pivot; said adjustable abutment pivot having an apical end and an occlusal end;
   i. said apical end defines a pivot mounting member for mounting and securely coupling said pivot with the dental implant anchor with at least one coupling portion selected from the group consisting of: threading, Morse angle, friction fit, snap fit, and any combination thereof; said pivot mounting member comprising a tooling interface provided to facilitate maneuvering said pivot with optional tools;
   ii. said occlusal end extending from and continuous with said pivot mounting member forming a pivot projection, said pivot projection is a malleable rod characterized in that said rod may be individually customized to provide a desired vertical dimension in the vertical plane relative to said mounting member and a desired angle in any direction in the occlusal plane; said pivot projection further comprises a plurality of adjustable portions and engaging portions along the length of said pivot projection; said adjustable portions are disposed between said engaging portions, said adjustable portions are provided to adjust the length and angular position of said pivot projection relative to said apical end of said pivot; said engaging portions feature external threading having the same thread parameters; and
b. an interface member, the interface member provided for coupling with the implanted dental implant anchor along the implant's internal connection platform, the interface member is a hollow tubular member featuring a non-customizable distal portion and a customizable proximal portion forming a lumen defined along its length between the distal portion and proximal portion; wherein said lumen is configured to receive said adjustable abutment pivot and filling material:
   i. the distal portion defining a non-customizable anchor coupling interface having an external surface for matching and internally fitting within the implant anchor's internal connection platform;
   ii. the proximal portion having an elevated rim configured to be customizable so as to assume a shape, angle and vertical dimension according to an individual's gingival morphology wherein once customized said elevated rim defines a trans-gingival collar of the abutment assembly and an upper end thereof defining a shoulder on which a restoration is supported;
said abutment assembly is characterized in that all of its members are customizable by a practitioner, according to an individual's gingival morphology and prosthodontic requirements of a patient, wherein said customization is provided at a proximal or occlusal end of said abutment assembly members, wherein the proximal and occlusal ends are customized to be provided with at least one of a desired surface, angle, or vertical dimension.

2. The abutment assembly of claim 1 wherein said assembly further includes at least one sleeve member, wherein said at least one sleeve member is provided for defining the external surface of said customized abutment.

3. The abutment assembly of claim 2 wherein said interface member receives:
   a. said adjustable pivot therein interfacing with said pivot along a pivot mounting member portion that is provided for mounting and securely coupling said pivot with the implanted dental implant anchor,
   b. an apical end of said at least one sleeve member, and
   c. said filling material for affixing said adjustable pivot, said at least one sleeve member's apical end, all within said lumen.

4. The abutment assembly of claim 2 wherein said sleeve member has substantially parallel opposite external walls, said sleeve member comprising:
   a. an apical end configured to be associated with said proximal portion of said interface member in a manner selected from at least one of: placed within said hollow interface member, or along the external surface of the elevated rim of said interface member, or on the upper surface of said elevated rim that defines a flange of said interface member;
   b. an occlusal end configured to interface with at least one of: a locking nut, a restoration, or a prosthodontic attachment; and
   c. a passage there between defining a sleeve lumen configured to receive and house at least one selected from: other sleeve members, a filling material and at least a portion of said adjustable pivot.

5. The abutment assembly of claim 4 wherein said apical end of said sleeve member has a larger external diameter then the external diameter of said occlusal end of said sleeve member therein defining a disc like configuration about said apical end of said sleeve.

6. The abutment assembly of claim 4 wherein at least a portion of said sleeve lumen comprises threading configured to correspond with and couple with said threading disposed along a portion of said adjustable pivot.

7. The abutment assembly of claim 4 wherein said sleeve is provided with a surface profile selected from the group consisting of: a flat surface, hourglass shape, polygonal surface of n sides (where n is at least 3), oval, cylindrical with changing diameter about its length, hyperboloid and ellipsoid, or any combination thereof.

8. The abutment assembly of claim 4 wherein said sleeve member may be made of biocompatible materials selected from the group consisting of plastics, carbon fiber, fiberglass, acrylics, polymers, antibacterial metals or alloys thereof, titanium, titanium alloy, tantalum, tantalum alloy, zirconium, or any combination thereof.

9. The abutment assembly of claim 2 wherein said sleeve member is configured to be integrated with said restoration, wherein said sleeve member forms a restoration mounting bore for said restoration that is to be associated with said customized abutment assembly, wherein said sleeve defines an inner surface and margins of said restoration's receiving bore.

10. The abutment assembly of claim 2 including two of said sleeve members that are configured to be telescopically associated with one another, wherein said telescopic association is provided by way of friction fitting or suction between said two sleeve members.

11. The abutment assembly of claim 10 wherein said two sleeve members are configured to form a sleeve assembly including an inner sleeve member and an external sleeve member, wherein said inner sleeve member defines the external surface of said customized abutment and said external sleeve member defines the inner surface of the restoration along its receiving bore.

12. The abutment assembly of claim 1 wherein said pivot is provided from at least two individual of said adjustable and engaging portions that are coupled with one another.

13. The abutment assembly of claim 1 wherein said adjustable and engaging portions of said adjustable abutment pivot are provided in a configuration selected from the group consisting of ball and socket joints, elastic rods, interlocking joints, and springs.

14. The abutment assembly of claim 1 wherein said pivot mounting member further comprising a cylindrical stabilizing portion utilized to stabilize said abutment pivot and to lock said abutment pivot and said interface member with said anchor.

15. The abutment assembly of claim 12 wherein the pivot mounting member and the pivot projection define said at least two individual members that are coupled with one another over a ball and socket joint arrangement comprising a seat member and corresponding ball member, wherein either of said ball and socket joint arrangement members may be disposed on either of said at least two individual members.

16. The abutment assembly of claim 15 wherein said seat member of said ball and socket joint arrangement is provided in the form of a tilt limiting seat provided to limit the range of motion of said ball and socket joint.

17. The abutment assembly of claim 1 wherein the length of said pivot projection may be extended with a pivot extending member, said extending member including:
   a. a pivot coupling member having threading configured to couple with at least one engaging portions having said threading that is disposed on said pivot projection; and
   b. an extension portion including a malleable rod extending from said coupling member, said malleable rod characterized in that said rod may be individually customized according to an individual's gingival morphology to provide a desired vertical dimension in the vertical plane relative to said coupling member and a desired angle in any direction in the occlusal plane.

18. The abutment assembly of claim 2 further comprising at least one abutment assembly member selected from the group consisting of a locking nut member, a pivot extending member or any combination thereof.

19. The abutment assembly of claim 18 wherein said locking nut member comprises:
   a. an apical end configured to interface with at least one of said sleeve or said adjustable abutment pivot, said apical end comprises a stepped centering surface said centering surface provided to interface with an occlusal portion of said at least one sleeve member within a sleeve lumen;
   b. a restoration end defining a tooling surface provided to manipulate said locking nut; and
   c. wherein said locking nut comprises threaded lumen defined between said apical end and said restoration end, said threaded lumen having threading corresponding to said threading disposed along said engaging portion of said adjustable pivot.

20. The abutment assembly of claim 1 wherein said elevated rim of said interface member has a height of at least 0.5 mm and up to 7 mm and wherein said proximal portion of said interface member has a diameter that is at least equal to or larger than the diameter of said distal portion of said interface member.

* * * * *